United States Patent [19]

Ferrand et al.

[11] Patent Number: 5,001,134
[45] Date of Patent: Mar. 19, 1991

[54] PIPERIDINES, PROCESSES OF PREPARATION AND MEDICATIONS CONTAINING THEM

[75] Inventors: Gérard Ferrand, Lyons; Hervé Dumas, Villefontaine; Jean-Claude Depin, Lyons; Gilles Chavernac, La Mulatiere, all of France

[73] Assignee: Lipha, Lyonnaise Industrielle Pharmaceutique, Lyons, France

[21] Appl. No.: 461,515

[22] Filed: Jan. 5, 1990

[30] Foreign Application Priority Data

Jan. 5, 1989 [FR] France ................ 89 00071

[51] Int. Cl.⁵ ............... C07D 413/04; C07D 211/32; A61K 31/445; A61K 31/42
[52] U.S. Cl. .................. 514/321; 514/316; 514/326; 514/330; 546/187; 546/189; 546/198; 546/225; 546/207
[58] Field of Search ............ 546/198, 225, 187, 189, 546/207; 514/330, 316, 321, 326

[56] References Cited

U.S. PATENT DOCUMENTS 4,355,037 10/1982 Strupczewski et al. ............ 546/225

FOREIGN PATENT DOCUMENTS 0196132 3/1985 European Pat. Off. .
WO83/4022 11/1983 PCT Int'l Appl. .

Primary Examiner—Mary C. Lee
Assistant Examiner—Lenora Mittenberger
Attorney, Agent, or Firm—Browdy and Neimark

[57] ABSTRACT

The present invention relates to piperidines denoted by the formula:

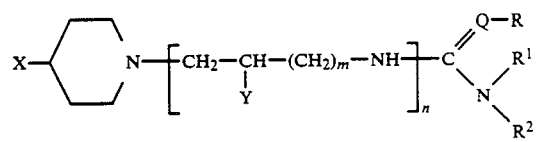

in which X is the 4-fluorobenzoyl, 2-(4-fluorophenyl)-1,3-dioxolan-2-yl or 6-fluoro-1,2-benzisoxazol-3-yl group, Y is a hydrogen atom or the hydroxyl group, m is an integer between 0 and 4 inclusive, n is 0 or 1, Q is a nitrogen atom or the methine group; when Q is a nitrogen atom, R is the cyano group or the carbamoyl group; when Q is the methine group, R is the nitro group; $R^1$ and $R^2$ may be identical or different and are hydrogen, a lower alkyl radical, the phenyl radical, the 2,2,2-trifluoroethyl group or the 2-[4-(4-fluorobenzoyl)-1-piperidinyl]ethyl group; or the $NR^1R^2$ structural unit is the piperidino radical or the 4-(4-fluorobenzoyl)-1-piperidinyl group.

Application of these compounds as antihypertensive medications.

16 Claims, No Drawings

PIPERIDINES, PROCESSES OF PREPARATION AND MEDICATIONS CONTAINING THEM

BACKGROUND OF THE INVENTION

The present invention relates to piperidines, to processes allowing them to be prepared and to their application in the field of therapeutics.

DESCRIPTION OF THE PRIOR ART

The part possibly played by serotoninergic receptors in association with the adrenergic receptors in the treatment of certain cardiovascular disorders and in particular of hypertension, is illustrated by 3-[2-[4-(4-fluorobenzoyl)-1-piperidinyl]ethyl]quinazolin-2,4(1H,3H)dione, known by the name of ketanserin. The action of 3-[2-[4-(6-fluoro-1,2-benzisoxazol-3-yl)-1-piperidinyl]ethyl]-2-methyl-6,7,8,9-tetrahydro-4H-pyrido[1,2-a]pyrimidin-4-one, described by L. E. J. Kennis and J. Vandenberk in European Patent No. 196,132, and known by the name of risperidone, on the serotoninergic receptors is also known. Furthermore, J. P. Cornu et al. have described, in Patent No. WO 83/04.022, the antihypertensive, vasodilatary and sedative actions of piperidines substituted by a phenyloxoalkyl group on the nitrogen atom, like, for example, N-cyano-N'-[[1-[4-(4-fluorophenyl)-4-oxobutyl]-4-piperidinyl]methyl]-N"-methylguanidine.

SUMMARY OF THE INVENTION

The compounds which are the subjects of the invention are denoted by the general formula I

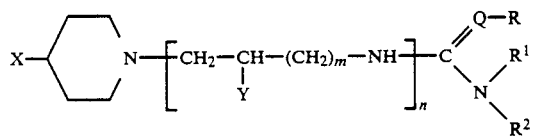

is the 4-fluorobenzoyl, 2-(4-fluorophenyl)-1,3-dioxolan-2-yl or 6-fluoro-1,2-benzisoxazol-3-yl group, Y is a hydrogen atom or the hydroxyl group, m is an integer between 0 and 4 inclusive, n is 0 or 1, Q is a nitrogen atom or the methine group; when Q is a nitrogen atom, R is the cyano group or the carbamoyl group; when Q is the methine group, R is the nitro group; $R^1$ and $R^2$ may be identical or different and are hydrogen, a lower alkyl radical, the phenyl radical or the 2,2,2-trifluoroethyl or the 2-[4-(4-fluorobenzoyl)-1-piperidinyl]ethyl group; or the $NR^1R^2$ structural unit is the piperidino radical or the 4-(4-fluorobenzoyl)-1-piperidinyl group.

The term lower applied to an alkyl radical means that the radical may be linear or branched and that it may contain from 1 to 6 carbon atoms.

The possible tautomeric forms of the compounds of the invention form an integral part of the invention.

The compounds in whose formula X is the 4-fluorobenzoyl or 6-fluoro-1,2-benzisoxazol-3-yl group, Y is a hydrogen atom, m is equal to 0, 1 or 2 and n is equal to 1 constitute a class of particular interest.

The pharmaceutically acceptable salts also form an integral part of the invention. These may be salts prepared either from inorganic acids such as hydrochloric acid, hydrobromic acid, sulfuric acid, phosphoric acid, or from organic acids such as tartaric acid, citric acid, acetic acid, maleic acid, fumaric acid, oxalic acid and methanesulfonic acid.

DESCRIPTION OF THE PREFERRED EMBODIMENTS

The compounds of the invention can be prepared according to at least one of the following methods:

(a) An amine of formula II

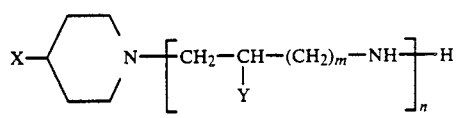

is condensed with a derivative of formula III

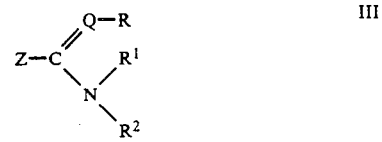

In the formulae II and III, X, Y, Q, R, $R^1$, $R^2$, m and n have the meanings given above. In formula III, Z denotes a group which is easily displaceable by an amine and is preferably a methylthio radical or a phenoxy radical. The reaction is carried out in an inert solvent. The preferred solvents are alkanols of low molecular weight, in particular ethanol and 2-methoxyethanol. The temperature may vary between the room temperature and the boiling temperature of the solvent employed. The reaction time is generally between 3 and 40 hours.

(b) A derivative of formula IV

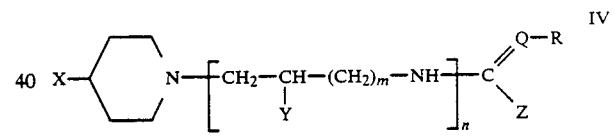

is condensed with an amine of formula V

In the formulae IV and V, X, Y, Q, R, $R^1$, $R^2$, m and n have the meanings given above In formula IV, Z denotes a group which is easily displaceable by an amine and is preferably a methylthio radical or a phenoxy radical. This condensation is carried out either without solvent in the presence of an excess of amine of formula V, or in an inert solvent. The preferred solvents are alkanols of low molecular weight, in particular ethanol. The temperature may vary between the room temperature and the boiling temperature of the amine of formula V or of the solvent employed. Reaction time is between 1 and 22 hours.

(c) In the particular case where X is the 4-fluorobenzoyl group, Q a nitrogen atom and R the carbamoyl group, the corresponding compounds of the invention I may be obtained by hydrolysis of the compounds I in which X is the 2-(4-fluorophenyl)-1,3-dioxolan-2-yl group, Q is a nitrogen atom and R is the cyano group.

(d) In the particular case where X is the 6-fluoro-1,2-benzisoxazol-3-yl group, Q a nitrogen atom and R the carbamoyl group, the corresponding compounds of the invention I are obtained by hydrolysis of the compounds I in which X is the 6-fluoro-1,2-benzisoxazol-3-yl group, Q is a nitrogen atom and R is the cyano group.

Some of the intermediate amines of general formula II are known compounds. Those which are new were prepared according to the usual techniques:

(α) When X is the 4-fluorobenzoyl or 2-(4-fluorophenyl)-1,3-dioxolan-2-yl group, Y a hydrogen atom and when m is equal to 1 and n is equal to 1, the corresponding amines VIII and IX are obtained according to the following reaction scheme:

of formula VIII. The acetal functional group of compound VIII can be hydrolysed in an acidic medium to give 1-(3-aminopropyl)-4-(4-fluorobenzoyl)piperidine of formula IX.

(β) When X is the 4-fluorobenzoyl or 2-(4-fluorophenyl)-1,3-dioxolan-2-yl group, Y a hydrogen atom and when m is equal to 4 and n is equal to 1, the corresponding amines XI and XII are obtained according to the reaction scheme below:

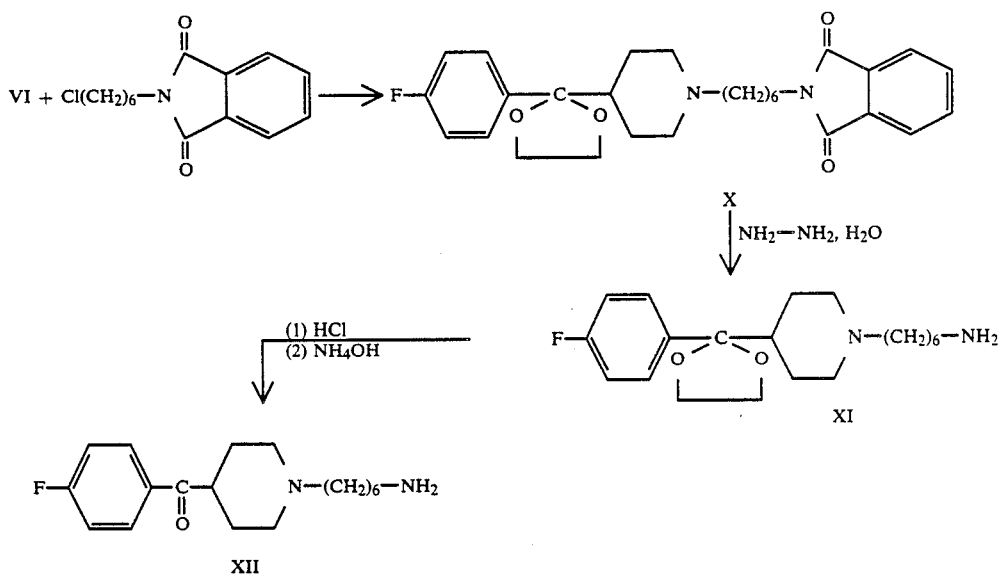

The piperidine VI is condensed with N-(6-chlorohexyl)phthalimide in the presence of a base such as an alkali metal carbonate, preferably potassium carbonate, to give a compound of formula X. On being treated with hydrazine hydrate, the N-alkylphthalimide X gives a 1-(6-aminohexyl)piperidine of formula XI. The acetal

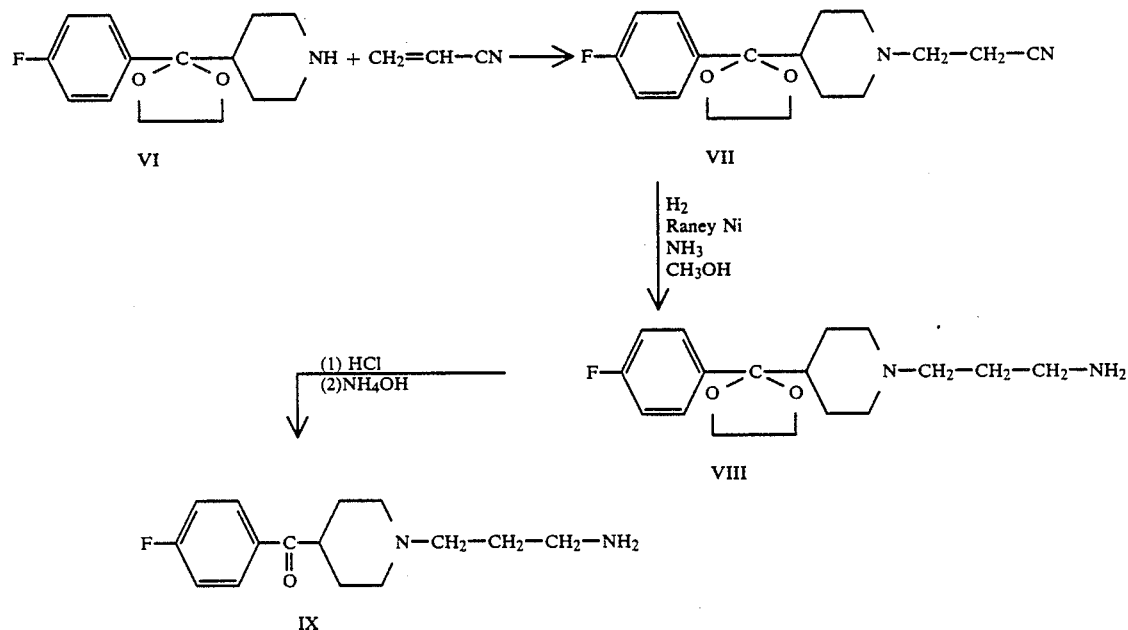

The piperidine VI reacts with acrylonitrile to give a 3-piperidinopropionitrile of formula VII which is then reduced catalytically to a 1-(3-aminopropyl)piperidine functional group of the compound XI can be hydrolysed in acidic medium to yield 1-(6-aminohexyl)-4-(4-fluorobenzoyl)piperidine of formula XII.

(γ) When X is the 4-fluorobenzoyl or 2-(4-fluorophenyl)-1,3-dioxolan-2-yl group, Y the hydroxyl group and when m is equal to 1 and n is equal to 1, the corresponding amines XIV and XV are obtained according to the reaction scheme below:

amino-2-hydroxypropyl)piperidine of formula XIV by a Gabriel synthesis. The acetal functional group of the compound XIV can be hydrolysed in acidic medium to yield 1-amino-3-[4-fluorobenzoyl)-1-piperidinyl]propan-2-ol of formula XV.

(δ) When X is the 6-fluoro-1,2-benzisoxazol-3-yl group, Y a hydrogen atom and when n is equal to 1, the

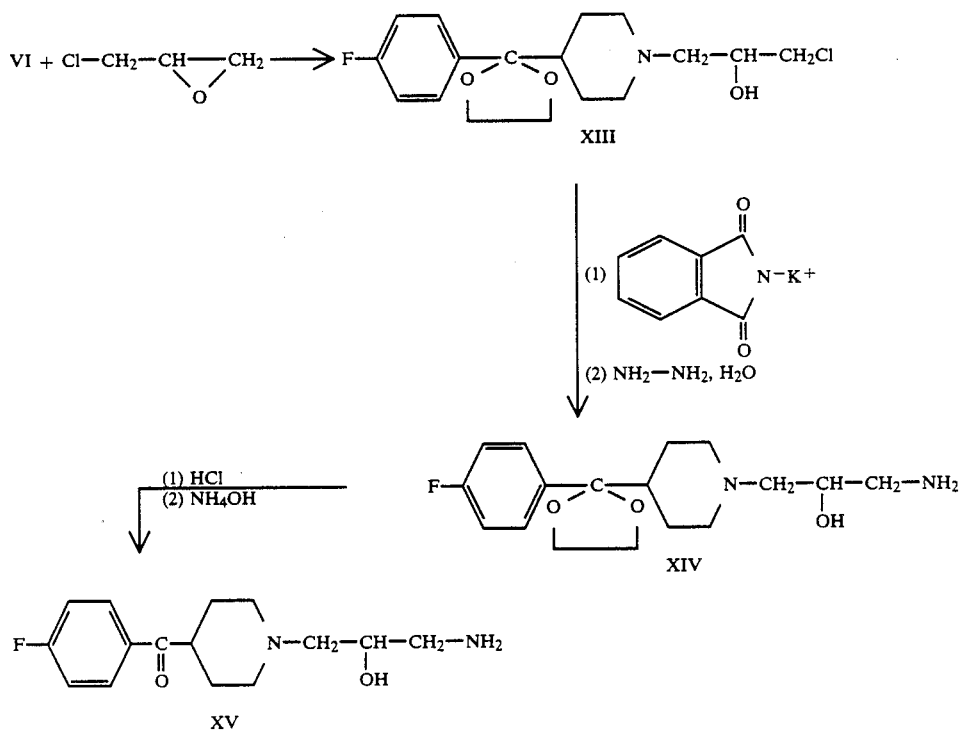

The piperidine VI is treated with epichlorohydrin to give the chlorinated compound of formula XIII. 1-(3-Chloro-2-hydroxypropyl)piperidine XIII gives a 1-(3- corresponding amines XIX are obtained according to the reaction scheme below:

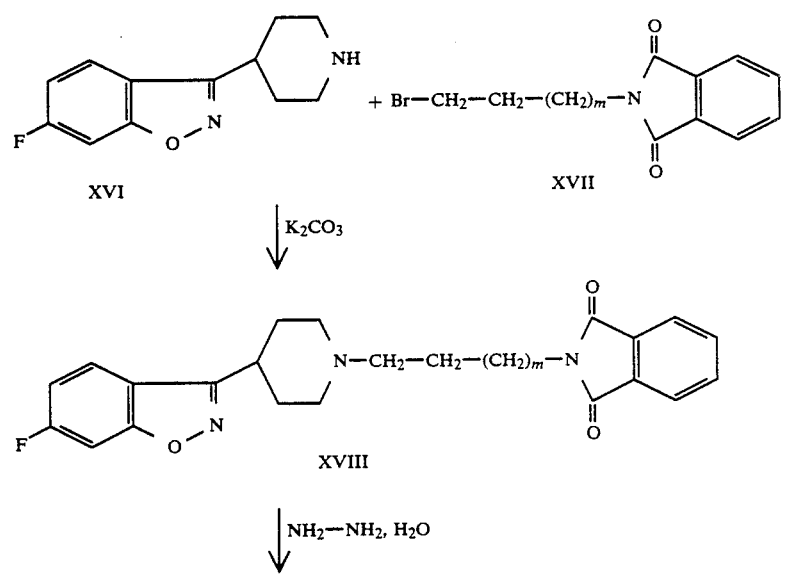

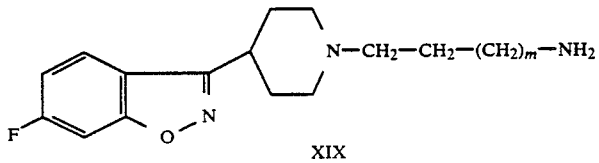

The piperidine XVI reacts with an N-(ω-bromoalkyl)phthalimide XVII in the presence of a base such as potassium carbonate, to give a phthalimide of formula XVIII, which is then converted by hydrazinolysis into a 3-[1-(ω-aminoalkyl)-4-piperidinyl]-6-fluoro-1,2-benzisoxazole of formula XIX. In the particular case where X is the 6-fluoro-1,2-benzisoxazol-3-yl group, Y a hydrogen atom and where m is equal to 1 and n is equal to 1, the corresponding amine XXII can also be obtained according to the reaction scheme below:

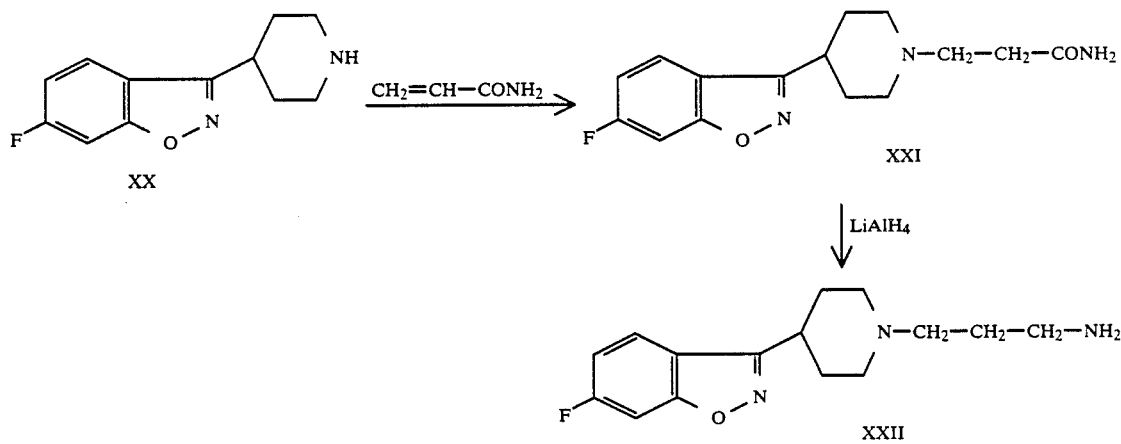

The piperidine XX reacts with acrylamide in an inert solvent such as ethanol, to give the propionamide of formula XXI, which is then reduced by a hydride such as lithium aluminium hydride to 3-[1-(3-aminopropyl)-4-piperidinyl]-6-fluoro-1,2-benzisoxazole of formula XXII.

In the particular case where X is the 6-fluoro-1,2-benzisoxazol-3-yl group, Y a hydrogen atom and where m is equal to zero and n is equal to 1, the corresponding amine XXIV can also be obtained by reduction of the acetonitrile of formula XXIII according to the following reaction:

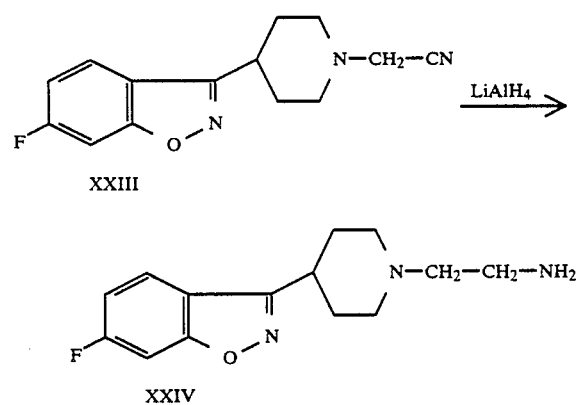

The intermediate derivates of formula III are in most cases those of known compounds. Those which are new were prepared according to the usual techniques, namely: when Q is a nitrogen atom, R the cyano group and Z the methylthio radical, the corresponding derivatives of formula III are obtained by condensing the amines of formula V with dimethyl N-cyanodithioiminocarbonate. In formula V, $R^1$ and $R^2$ have the meanings given above.

The intermediate derivatives of formula IV are new products. They are prepared by condensing an amine of formula II with a derivative of formula XXV.

In formulae II and XXV the substituents X, Y, Q, R and m and n have the meanings given above In formula XXV, Z denotes a group which is easily displaceable by an amine and is preferably a methylthio radical or a phenoxy radical.

The compounds denoted by the general formula I have remarkable antihypertensive and antiserotonin properties liable to make their use particularly advantageous in the hypertensive disease as well as in organic disorders engendered or aggravated by an excess of serotonin.

The antihypertensive activity was investigated in the genetically hypertensive rat (SHR) whose arterial pressure was regularly monitored: hypertensive male rats having a particularly stable arterial pressure are grouped by 10 and treated orally with the compounds being studied Their arterial pressure is measured 3 hours later. The minimum dose significantly reducing the mean arterial pressure of the treated group (M.A.D.) is thus determined for each compound.

The antagonism towards serotonin was demonstrated in vitro on the isolated rat aorta: male rats of approximately 300 g are sacrificed and bled. The thoracic aorta is rapidly removed. A fragment of approximately 1 cm is cut into a spiral and then placed in a cell containing 20 ml of nutrient medium (Krebs-Henseleit) kept at 37° C. and oxygenated (95% $O_2$, 5% $CO_2$). The contraction is recorded using an isotonic strain gauge. After a rest of 45 min, supramaximal contractions are triggered by adding serotonin (20 μM) to the survival medium. A plateau is generally reached after 10 min of contact, the latter not exceeding 25 min. A rest of 30 min and numerous rinsings separate each contraction. The products are added 10 min after the serotonin and left for 15 min, at the end of which period the inhibition is measured. The inhibiting concentration 50 (IC 50) is determined for each compound being studied on a minimum of 3 aortas.

The results obtained by these two methods in the case of a few products of the invention and in the case of ketanserin (3-[2-[4-(4-fluorobenzoyl)-1-piperidinyl]ethyl]quinazolin-2,4-(1H,3H)-dione), taken as control, are listed in Table I.

TABLE I

| PRODUCTS | Antihypertensive activity (SHR) M.A.D. (mg/kg/PO) | Isolated rat aorta antiserotonin activity IC 50 (μM) |
|---|---|---|
| Ketanserin | 25 | 0.15 |
| Example 1 | 10 | 0.53 |
| Example 10 | 10 | 0.46 |
| Example 12 | 5 | 0.17 |
| Example 13 | 5 | 1.95 |
| Example 14 | 10 | 0.67 |
| Example 18 | 2 | 0.09 |
| Example 19 | 0.5 | 0.05 |
| Example 20 | 0.5 | 0.04 |
| Example 21 | 2 | 0.10 |
| Example 22 | 5 | 0.02 |
| Example 24 | 10 | 2.90 |
| Example 26 | 5 | 0.38 |

The compounds of the invention exhibit a low toxicity. By way of illustration, the 50 lethal dose determined on the rat using the oral route, in the case of the compound described in Example 1, is 1,700 mg/kg, that is 170 times the active dose in this species.

The application of the compounds I as medications and especially as antihypertensive medications is also a subject of the present application. These medications may be administered orally in the form of tablets, coated tablets or gelatin capsules or intravenously in the form of injectable solute. The active principle is associated with various pharmaceutically compatible excipients. The daily dosages may vary from 2 to 100 mg of active principle taken orally and from 0.2 to 10 mg of active principle taken intravenously.

A few pharmaceutical compositions are given below by way of examples, no limitation being implied:

| Composition of a tablet: | |
|---|---|
| active principle | 10 mg |
| excipient: lactose, wheat starch, polyvidone, talc, magnesium stearate. | |
| Composition of a gelatin capsule: | |
| active principle | 10 mg |
| excipient: lactose, wheat starch, talc, magnesium stearate. | |

The following examples illustrate the invention, no limitation being implied. In the nuclear magnetic resonance (N.M.R.) data, the following abbreviations have been used: s for singlet, d for doublet, t for triplet, q for quadruplet and m for unresolved peaks; the chemical shifts δ are expressed in ppm.

EXAMPLE 1

N-Cyano-N'-[-2-[4-(4-fluorobenzoyl)-1-piperidinyl]ethyl]-N''-methylguanidine (a)

N-Cyano-N'-[2-[4-(4-fluorobenzoyl)-1-piperidinyl]ethyl]-S-methylisothiourea

A solution of 5.7 g (0.023 moles of 1-(2-aminoethyl)-4-(4-fluorobenzoyl)piperidine [prepared according to A. Storni, European Patent No. 124,476; C.A. (1985) 102, 131917b] in 45 ml of ethanol is added dropwise to a solution of 3.3 g (0.023 moles) of dimethyl N-cyanodithioiminocarbonate in 52 ml of ethanol. Stirring is continued for 8 hours at room temperature after the end of the addition; a release of methyl mercaptan is produced. The reaction mixture is then cooled to about 0° C. The precipitate formed is isolated by filtration; it is washed with ether and recrystallized from ethanol. Yld: 5.5 g (69%), mp=137°-139° C.

Percentage analysis: $C_{17}H_{21}FN_4OS$ (FW=348.44)

| | C % | H % | F % | N % | S % |
|---|---|---|---|---|---|
| Calculated | 58.60 | 6.08 | 5.45 | 16.08 | 9.20 |
| Found | 58.78 | 5.94 | 5.30 | 16.13 | 9.45 |

IR:
$\nu$ (C=O) = 1670 cm$^{-1}$
$\nu$ (C≡N) = 2160 cm$^{-1}$
N.M.R. (CDCl$_3$): δ=2.5 (3H, s); 1.6-3.7 (13H, m); 6.7 (1H, peak exchangeable with D$_2$O); 7.0-7.4 (2H, m); 7.8-8.2 (2H, m).

(b)

N-Cyano-N'-[2-[4-(4-fluorobenzoyl)-1-piperidinyl]ethyl-N''-methylguanidine 32 ml of a solution containing 33% of methylamine in absolute ethanol are added dropwise to a suspension of 5.5 g (0.016 moles) of N-cyano-N'-[2-[4-(4-fluorobenzoyl)-1-piperidinyl]ethyl]-S-methylisothiourea in 32 ml of ethanol. The solution obtain is heated under reflux for 1 hour. A release of methyl mercaptan is produced. After cooling, the precipitate formed is filtered off, washed with hexane and dried. It is recrystallized from ethanol. Yld: 4.3 g (82%), mp=160°-162° C.

Percentage analysis: $C_{17}H_{22}FN_5OS$ (FW=331.39)

| | C % | H % | F % | N % |
|---|---|---|---|---|
| Calculated | 61.61 | 6.69 | 5.73 | 21.14 |
| Found | 61.79 | 6.49 | 5.46 | 21.26 |

IR:
$\nu$ (C=O) = 1670 cm$^{-1}$
$\nu$ (C≡N) = 2160 cm$^{-1}$
N.M.R. (CDCl$_3$+DMSO-d$_6$): δ=2.7 (3H, d is converted into s with D$_2$O); 1.4-3.7 (13H, m); 6.3 (1H, peak exchangeable with D$_2$O); 6.9-7.4 (2H, m); 7.7 (1H, peak exchangeable with D$_2$O); 7.8-8.2 (2H, m).

EXAMPLE 2

N-Cyano-N'-[2-[4-(4-fluorobenzoyl)-1-piperidinyl]ethyl]-N''-methylguanidine (a)

N-Cyano-N'-[2-[4-(4-fluorobenzoyl)-1-piperidinyl]ethyl]phenoxyformamidine

A mixture of 9.5 g (0.040 moles) of diphenyl N-cyanocarbonimidate and of 10.0 g (0.040 moles) of 1-(2-aminoethyl)-4-(4-fluorobenzoyl)piperidine in 100 ml of isopropanol is stirred for 15 hours at room temperature. The precipitate formed is isolated by filtration; it is washed with ether and recrystallized from ethyl acetate. Yld: 11.0 g (70%), mp=134°-136° C.

Percentage analysis: $C_{22}H_{23}FN_4O_2$ (FW = 394.45)

|  | C % | H % | F % | N % |
| --- | --- | --- | --- | --- |
| Calculated | 66.99 | 5.88 | 4.82 | 14.20 |
| Found | 66.93 | 5.82 | 4.83 | 14.08 |

IR:

$\nu$ (C=O) = 1655 cm$^{-1}$
$\nu$ (C≡N) = 2175 cm$^{-1}$

N.M.R. (CDCl$_3$+D$_2$O): $\delta$ = 1.5-3.8 (13H, m); 6.9-7.6 (7H, m); 7.7-8.1 (2H, m).

(b)

N-Cyano-N'-[2-[4-(4-fluorobenzoyl)-1-piperidinyl]ethyl]-N''-methylguanidine 5.4 ml of a solution containing 33% of methylamine in absolute ethanol is added dropwise to a suspension of 2.1 g (0.0053 moles) of N-cyano-N'-[2-[4-(4-fluorobenzoyl)-1-piperidinyl]ethyl]phenoxyformamidine in 25 ml of ethanol. The solution obtained is stirred for 1 hour at room temperature. The reaction mixture is then cooled to about 0° C. The precipitate formed is isolated by filtration; it is washed with ether and recrystallized from ethanol. Yld: 1.3 g (74%), mp 160°-162° C. The product is identical with that obtained in Example 1.

EXAMPLE 3

N-Cyano-N'-[2-[4-[2-(4-fluorophenyl)-1,3-dioxolan-2-yl]-1-piperidinylethyl]-N''-methylguanidine A mixture of 10.4 g (0.035 moles) of 1-(2-aminoethyl)-4-[2-(4-fluorophenyl)-1,3-dioxolan-2-yl]piperidine [prepared according to J. Vandenberk et al., European Patent No. 184,258; C.A. (1986) 105, 133907j] and of 4.5 g (0.035 moles) of N-cyano-N'-methyl-S-methylisothiourea in 120 ml of 2-methoxyethanol is heated under reflux for 3 hours. A release of methyl mercaptan is produced. After cooling, the solution obtained is concentrated to dryness under reduced pressure. The solid residue is washed with ether and recrystallized from ethanol. Yld: 4.1 g (31%), mp=194°-196° C.

Percentage analysis: $C_{19}H_{26}FN_5O_2$ (FW = 375.44)

|  | C % | H % | F % | N % |
| --- | --- | --- | --- | --- |
| Calculated | 60.78 | 6.98 | 5.06 | 18.65 |
| Found | 60.75 | 6.93 | 4.99 | 18.71 |

IR:

$\nu$ (C≡N) = 2150 cm$^{-1}$

N.M.R. (DMSO-d$_6$+CF$_3$COOD): $\delta$ = 2.7 (3H, s); 1.2-3.6 (13H, m); 3.4-4.1 (4H, m); 6.8-7.5 (4H, m).

EXAMPLE 4

N-Cyano-N'-[2-[4-[2-(4-fluorophenyl)-1,3-dioxolan-2-yl]-1-piperidinyl]ethyl]guanidine A mixture of 4.0 g (0.0136 moles) of 1-(2-aminoethyl)-4-[2-(4-fluorophenyl)-1,3-dioxolan-2-yl]piperidine and of 1.6 g (0.0136 moles) of N-cyano-S-methylisothiourea [prepared according to C. G. McCarty et al., J. Org. Chem. (1970) 35, 2067] in 100 ml of 2-methoxyethanol is heated under reflux for 16 hours. A release of methyl mercaptan is produced. After cooling, the reaction mixture is concentrated to dryness under reduced pressure. The residue is chromatographed on a silica column. Eluent: chloroform/methanol: 4/1. Evaporation of the eluate yields N-cyano-N'-[2-[4-[2-(4-fluorophenyl)-1,3-dioxolan-2-yl]-1-piperidinyl]ethyl]guanidine. Yld: 1.0 g (20%), mp=161°-163° C. (ethanol-isopropyl ether).

Percentage analysis: $C_{18}H_{24}FN_5O_2$ (FW = 361.42)

|  | C % | H % | F % | N % |
| --- | --- | --- | --- | --- |
| Calculated | 59.82 | 6.69 | 5.26 | 19.38 |
| Found | 59.55 | 6.65 | 4.92 | 19.46 |

IR:

$\nu$ (C≡N) = 2150 cm$^{-1}$

N.M.R. (CDCl$_3$+CF$_3$COOD): $\delta$ = 1.5-3.7 (13H, m); 3.5-4.1 (4H, m); 6.7-7.5 (4H, m).

EXAMPLE 5

N-Cyano-N'-[2-[4-[2-(4-fluorophenyl)-1,3-dioxolan-2-yl]-1-piperidinyl]ethyl]guanidine (a)

N-Cyano-N'-[2-[4-[2-(4-fluorophenyl)-1,3-dioxolan-2-yl]-1-piperidinyl]ethyl]-S-methylisothiourea A solution of 12.0 g (0.041 moles) of 1-(2-aminoethyl)-4-[2-(4-fluorophenyl)-1,3-dioxolan-2-yl]piperidine in 80 ml of ethanol is added dropwise to a solution of 6.0 g (0.041 moles) of dimethyl N-cyanodithioiminocarbonate in 100 ml of ethanol. Stirring is continued for 9 hours at room temperature after the end of the addition; a release of methyl mercaptan is produced. The solution obtained is then concentrated to dryness under reduced pressure. The residue is washed with isopropyl ether and recrystallized from a mixture of ethanol and isopropyl ether. Yld: 12.1 g (75%), mp=133°-134.5° C.

Percentage analysis: $C_{19}H_{25}FN_4O_2S$ (FW = 392.49)

|  | C % | H % | F % | N % | S % |
| --- | --- | --- | --- | --- | --- |
| Calculated | 58.14 | 6.42 | 4.84 | 14.27 | 8.17 |
| Found | 57.76 | 6.66 | 4.79 | 13.98 | 8.03 |

IR:

$\nu$ (C≡N) = 2160 cm$^{-1}$

N.M.R. (CDCl$_3$+D$_2$O): $\delta$ = 2.4 (3H, s); 1.3-3.6 (13H, m); 3.5-4.1 (4H, m); 6.8-7.5 (4H, m).

(b)

N-Cyano-N'-[2-[4-[2-(4-fluorophenyl)-1,3-dioxolan-2-yl]-1-piperidinyl]ethyl]guanidine A solution of 4.0 g (0.010 moles) of N-cyano-N'-[2-[4-[2-(4-fluorophenyl)-1,3-dioxolan-2-yl]-1-piperidinyl]ethyl]-S-methylisothiourea in 100 ml of ethanol is heated under reflux; a stream of ammonia is bubbled through this solution for 20 hours. After cooling, the reaction mixture is concentrated to dryness under reduced pressure. The residue is made concrete in a mixture of isopropyl ether and of isopropanol. It is purified by recrystallization from a mixture of ethanol and of isopropyl ether. Yld: 0.6 g (17%), mp=161°-163° C. The product is identical with that obtained in Example 4.

EXAMPLE 6

N-Cyano-N'-[2-[4-(4-fluorobenzoyl)-1-piperidinyl]ethyl]-N''-phenyl]guanidine

A mixture of 11.0 g (0.032 moles) of N-cyano-N'-[2-[4-(4-fluorobenzoyl)-1-piperidinyl]ethyl]-S-methylisothiourea and of 80 ml of aniline is heated to 110°-120° C. for 7 hours and then to 135° C. for 1 hour 45 min. A release of methyl mercaptan is produced. The reaction mixture is then concentrated to dryness under reduced pressure. The residue is purified by recrystallization from ethanol. Yld: 3.8 g (31%), mp=199°-201° C.

Percentage analysis: $C_{22}H_{24}FN_5O$ (FW=393.45)

|  | C % | H % | F % | N % |
|---|---|---|---|---|
| Calculated | 67.15 | 6.15 | 4.83 | 17.80 |
| Found | 67.00 | 6.21 | 4.88 | 17.84 |

IR:
$\nu$ (C=O)=1670 cm$^{-1}$
$\nu$ (C≡N)=2160 cm$^{-1}$

N.M.R. (DMSO-d$_6$30 CF$_3$COOD): $\delta$=1.4-2.3 (4H, m); 2.6-4.0 (9H, m); 6.9-7.5 (7H, m); 7.8-8.2 (2H, m).

EXAMPLE 7

N-Cyano-N'-[2-[4-(4-fluorobenzoyl)-1-piperidinyl]ethyl]-N''-isopropylguanidine

A mixture of 4.0 g (0.0115 moles) of N-cyano-N'-[2-[4-(4-fluorobenzoyl)-1-piperidinyl]ethyl]-S-methylisothiourea and of 40 ml of isopropylamine is heated under gentle reflux for 3 hours 30 min. 40 ml of ethanol are added and the mixture is heated under reflux for 3 hours. The release of methyl mercaptan is very gradual. 20 ml of isopropylamine are added and refluxing is continued for 8 hours. After cooling, the precipitate formed is isolated by filtration; it is washed with ether and recrystallized from a mixture of ethanol and isopropyl ether in the presence of Norit. Yld: 1.6 g (39%), mp=158°-160° C.

Percentage analysis: $C_{19}H_{26}FN_5O$ (FW=359.44)

|  | C % | H % | F % | N % |
|---|---|---|---|---|
| Calculated | 63.49 | 7.29 | 5.29 | 19.48 |
| Found | 63.33 | 7.15 | 5.25 | 19.25 |

IR:
$\nu$ (C=O)=1670 cm$^{-1}$
$\nu$ (C≡N)=2150 cm$^{-1}$

N.M.R. (DMSO-d$_6$): $\delta$=1.1 (6H, d); 1.2-4.1 (14H, m); 6.6 (1H, t exchangeable with CF$_3$COOD); 7.1 (1H, t exchangeable with CF$_3$COOD); 7.1-7.5 (2H, m); 7.8-8.2 (2H, m).

EXAMPLE 8

N-t-Butyl-N'-cyano-N''-[2-[4-(4-fluorobenzoyl)-1-piperidinyl]ethyl]guanidine

Obtained by operating as in Example 3, starting with 5.0 g (0.020 moles) of 1-(2-aminoethyl)-4-(4-fluorobenzoyl)piperidine and with 3.4 g (0.020 moles) of N-t-butyl-N'-cyano-S-methylisothiourea [prepared according to H. J. Pertersen, German Patent No. 2,557,438; C.A. (1976) 85, 42993e] in 120 ml of 2-methoxyethanol. Refluxing time: 37 hours. Yld: 1.6 g (21%), mp=81.5°-183.5° C. (ethanol).

Percentage analysis: $C_{20}H_{28}FN_5O$ (FW=373.47)

|  | C % | H % | F % | N % |
|---|---|---|---|---|
| Calculated | 64.32 | 7.56 | 5.09 | 18.75 |
| Found | 64.60 | 7.56 | 5.01 | 18.81 |

IR:
$\nu$ (C=O)=1665 cm$^{-1}$
$\nu$ (C≡N)=2150 cm$^{-1}$

N.M.R. (CDCl$_3$): $\delta$=1.4 (9H, s); 1.5-3.6 (13H, m); 5.6-6.1 (1H, m exchangeable with CF$_3$COOD); 6.2 (1H, peak exchangeable with CF$_3$COOD); 6.9-7.3 (2H, m); 7.7-8.1 (2H, m).

EXAMPLE 9

N-Cyano-N'-[2-[4-(4-fluorobenzoyl)-1-piperidinyl]ethyl-N''-(2,2,2-trifluoroethyl)guanidine (a)

N-Cyano-N'-(2,2,2-trifluoroethyl)-S-methylisothiourea

A mixture of 8.0 g (0.055 moles) of dimethyl N-cyanodithioiminocarbonate, of 8.1 g (0.060 moles) of 2,2,2-trifluoroethylamine hydrochloride and of 6.0 g (0.059 moles) of triethylamine in 75 ml of ethanol is heated to 40° C. for 7 hours. A release of methyl mercaptan is produced. 3.7 g (0.027 moles) of 2,2,2-trifluoroethylamine hydrochloride and 2.7 g (0.027 moles) of triethylamine are then added to the reaction mixture and heating to 40° C. is continued for 4 hours. The same quantities of reactants are added again and heating to 40° C. is continued for 3 more hours. After cooling, a very slight precipitate is removed by filtration. The filtrate is concentrated to dryness under reduced pressure. The residue is washed with water and recrystallized from ethanol. Yld: 4.9 g (45%), mp=151°-153° C.

Percentage analysis: $C_5H_6F_3N_3S$ (FW=197.18)

|  | C % | H % | F % | N % | S % |
|---|---|---|---|---|---|
| Calculated | 30.46 | 3.07 | 28.91 | 21.31 | 16.26 |
| Found | 30.58 | 3.21 | 28.98 | 21.18 | 16.43 |

IR:
$\nu$ (C≡N)=2160 cm$^{-1}$

N.M.R. (DMSO-d$_6$30 CF$_3$COOD): $\delta$=2.6 (3H, s); 4.2 (2H, q).

(b)

N-Cyano-N'-[2-[4-(4-fluorobenzoyl)-1-piperidinyl]ethyl]-N''-(2,2,2-trifluoroethyl)guanidine A solution of 2.8 g (0.011 moles) of 1-(2-aminoethyl)-4-(4-fluorobenzoyl)piperidine and of 2.2 g (0.011 moles) of N-cyano-N'-(2,2,2-trifluoroethyl)-S-methylisothiourea in 50 ml of ethanol is stirred for 4 hours at room temperature and then for 3 hours 30 min at about 55° C. and finally 14 hours 30 min at reflux. A release of methyl mercaptan is produced. The reaction mixture is then cooled to about 0° C. The precipitate formed is isolated by filtration; it is washed with ether and recrystallized from ethanol. Yld: 2.9 g (66%), mp=156°-158° C.

Percentage analysis: $C_{18}H_{21}F_4N_5O$ (FW=399.39)

|            | C %   | H %  | F %   | N %   |
|------------|-------|------|-------|-------|
| Calculated | 54.13 | 5.30 | 19.03 | 17.54 |
| Found      | 54.04 | 5.38 | 18.95 | 17.55 |

IR:
$\nu$ (C=O) = 1660 cm$^{-1}$
$\nu$ (C≡N) = 2150 cm$^{-1}$
N.M.R. (CDCl$_3$): $\delta$ = 1.5–3.5 (13H, m); 3.6–4.2 (2H, m is converted into q with D$_2$O); 6.6–7.0 (1H, m exchangeable with D$_2$O); 6.9–7.3 (2H, m); 7.7–8.2 (2H, m); 9.5–9.9 (1H, m exchangeable with D$_2$O).

EXAMPLE 10

N'-Cyano-N,N-dimethyl-N''-[2-[4-(4-fluorobenzoyl)-1-piperidinyl]ethyl]guanidine

Obtained by operating as in Example 4 starting with 5.0 g (0.020 moles) of 1-(2-aminoethyl)-4-(4-fluorobenzoyl)piperidine and with 4.4 g (0.030 moles) of N'-cyano-N,N-dimethyl-S-methylisothiourea [prepared according to B. T. Heitke and C. G. McCarty, J. Org. Chem. (1974) 39, 1522] in 110 ml of ethanol. Refluxing time: 34 hours. Chromatography eluent: methylene chloride/methanol: 95/5. Yld: 1.3 g (19%), mp = 139°–141° C. (ethanol-isopropyl ether).

Percentage analysis: C$_{18}$H$_{24}$FN$_5$O (FW = 345.42)

|            | C %   | H %  | F %  | N %   |
|------------|-------|------|------|-------|
| Calculated | 62.59 | 7.00 | 5.50 | 20.28 |
| Found      | 62.65 | 7.03 | 5.42 | 20.13 |

IR:
$\nu$ (C=O) = 1650 cm$^{-1}$
$\nu$ (C≡N) = 2150 cm$^{-1}$
N.M.R. (CDCl$_3$): $\delta$ = 1.5–3.2 (11H, m); 3.0 (6H, s); 3.5–3.9 (2H, m); 5.8 (1H, peak exchangeable with D$_2$O); 6.9–7.3 (2H, m); 7.7–8.2 (2H, m).

EXAMPLE 11

N-Cyano-N'-[3-[4-[2-(4-fluorophenyl)-1,3-dioxolan-2-yl]-1-piperidinyl]-propyl]-N''-ethyl]guanidine (a) 3-[4-[2-(4-Fluorophenyl)-1,3-dioxolan-2-yl]-1-piperidinyl]propionitrile 3.2 g (0.060 moles) of acrylonitrile are added dropwise to 12.6 g (0.050 moles) of 4-[2-(4-fluorophenyl)-1,3-dioxolan-2-yl]piperidine [prepared according to B. Dumaitre et al., European Patent No. 14,295; C.A. (1981) 94, 65699v], maintained between 55° and 60° C. After about 15 minutes a precipitate forms and is filtered off. The solid obtained is washed with hexane and dried. It is used in the next stage without other purification. Yld: 14.4 g (95%), mp = 107°–109° C.

N.M.R. (CDCl$_3$): $\delta$ = 1.1–3.1 (13H, m); 3.5–4.2 (4H, m); 6.8–7.5 (4H, m).

(b) 1-(3-Aminopropyl)-4-2-(4-fluorophenyl)-1,3-dioxolan-2-yl]piperidine

A mixture of 14.0 g (0.046 moles) of 3-[4-[2-(4-fluorophenyl)-1,3-dioxolan-2-yl]-1-piperidinyl]propionitrile, of 46 g of liquid ammonia and of 6 g of Raney nickel in 300 ml of methanol is introduced into an autoclave and hydrogenated at room temperature for 6 hours, the initial hydrogen pressure being set at 85 bars. After degassing, the reaction mixture is filtered and concentrated to dryness under reduced pressure. The residue is purified by distillation under reduced pressure. Yld: 12.1 g (85%), bp$_{1.5}$ = 168°–175° C.

N.M.R. (CDCl$_3$): $\delta$ = 1.2 (2H, s exchangeable with D$_2$O); 1.2–3.1 (15H, m); 3.5–4.1 (4H, m); 6.8–7.5 (4H, m).

(b) N-Cyano-N'-[3-4-[2-(4-fluorophenyl)-1,3-dioxolan-2-yl-1-piperidinyl]propyl-N''-methylguanidine Obtained by operating as in Example 3 starting with 10.0 g (0.032 moles) of 1-(3-aminopropyl)-4-[2-(4-fluorophenyl)-1,3-dioxolan-2-yl]piperidine and with 4.1 g (0.032 moles) of N-cyano-N'-methyl-S-methylisothiourea in 100 ml of 2-methoxyethanol. Yld: 4.5 g (36%), mp = 179°–181° C. (ethanol).

Percentage analysis: C$_{20}$H$_{28}$FN$_5$O$_2$ (FW = 389 47)

|            | C %   | H %  | F %  | N %   |
|------------|-------|------|------|-------|
| Calculated | 61.68 | 7.25 | 4.88 | 17.98 |
| Found      | 61.72 | 7.49 | 4.66 | 17.84 |

IR:
$\nu$ (C≡N) = 2150 cm$^{-1}$
N.M.R. (DMSO-d$_6$): 2.2 (1H, t exchangeable with CF$_3$COOD); 2.6 (3H, d is converted into s with CF$_3$COOD); 1.2–3.4 (15H, m); 3.4–4.1 (4H, m); 6.9 (1H, t exchangeable with CF$_3$COOD); 6.9–7.6 (4H, m).

EXAMPLE 12

N-Cyano-N'-[3-[4-(4-fluorobenzoyl)-1-piperidinyl]-propyl]-N''-methylguanidine (a) 1-(3-Aminopropyl)-4-(4-fluorobenzoyl)piperidine 52.5 g of 22% hydrochloric acid are added dropwise to a solution of 11.8 g (0.0382 moles) of 1-(3-aminopropyl)-4-[2-(4-fluorophenyl)-1,3-dioxolan-2-yl]piperidine in 100 ml of isopropanol. The mixture obtained is heated under reflux for 8 hours. After cooling, the reaction mixture is concentrated to dryness under reduced pressure. The residue is dissolved in 100 ml of water; this aqueous solution is made basic with aqueous ammonia and is extracted with methylene chloride. The combined organic extracts are dried over sodium sulfate and are concentrated to dryness under reduced pressure. The residue is used in the next stage without further purification. Yld: 10.6 g (quantitative).

N.M.R. (CDCl$_3$): $\delta$ = 1.5–3.6 (17H, m); 6.8–7.4 (2H, m); 7.7–8.2 (2H, m).

(b) N-Cyano-N'-3-4-(4-fluorobenzoyl)-1-piperidinyl]-propyl]-N''-methylguanidine

Obtained by operating as in Example 4 starting with 10.1 g (0.0382 moles) of 1-(3-aminopropyl)-4-(4-fluorobenzoyl)piperidine and with 4.7 g (0.0362 moles) of N-cyano-N'-methyl-S-methylisothiourea in 100 ml of 2-methoxyethanol. Refluxing time: 5 hours 30 min. Chromatography eluent: 98 methylene chloride - 2 methanol. Yld: 3.7 g (30%), mp = 171°–174° C. (ethanol).

Percentage analysis C$_{18}$H$_{24}$FN$_5$O (FW = 345.42)

|            | C %   | H %  | F %  | N %   |
|------------|-------|------|------|-------|
| Calculated | 62.59 | 7.00 | 5.50 | 20.27 |

|           | C %   | H %  | F %  | N %   |
|-----------|-------|------|------|-------|
| Found     | 62.40 | 7.22 | 5.30 | 20.09 |

IR:
$\nu$ (C=O) = 1665 cm$^{-1}$
$\nu$ (C≡N) = 2150 cm$^{-1}$
N.M.R. (DMSO-d$_6$): δ = 2.3 (1H, t exchangeable with CF$_3$COOD); 2.7 (2H, d is converted into s with CF$_3$COOD); 1.4–3.8 (15H, m); 7.0 (1H, t exchangeable with CF$_3$COOD); 7.1–7.6 (2H, m); 7.8–8.3 (2H, m).

EXAMPLE 13

N'-Cyano-N,N-dimethyl-N''-3-4-(4-fluorobenzoyl)-1-piperidinyl]propyl]guanidine

Obtained by operating as in Example 4 starting with 7.8 g (0.0295 moles) of 1-(3-aminopropyl)-4-(4-fluorobenzoyl)piperidine and 3.5 g (0.0244 moles) of N'-cyano-N,N-dimethyl-S-methylisothiourea in 100 ml of ethanol. Refluxing time: 12 hours. Chromatography eluent: methylene chloride/methanol: 9/1. Yld: 3.6 g (41%), mp = 89°–92° C. (ethanol-ethyl ether).

Percentage analysis: C$_{19}$H$_{26}$FN$_5$O (FW = 359.45)

|            | C %   | H %  | F %  | N %   |
|------------|-------|------|------|-------|
| Calculated | 63.49 | 7.29 | 5.29 | 19.48 |
| Found      | 63.26 | 7.33 | 5.16 | 19.35 |

IR:
$\nu$ (C=O) = 1650 cm$^{-1}$
$\nu$ (C≡N) = 2150 cm$^{-1}$
N.M.R. (CDCl$_3$): δ = 1.5–3.9 (21H, m) including 3.0 (6H, s) and 3.6 (2H, m is converted into t by D$_2$O); 6.8–7.5 (3H, m including 1H exchangeable with D$_2$O); 7.7–8.2 (2H, m).

EXAMPLE 14

N-Cyano-N'-[4-[4-(4-fluorobenzoyl)-1-piperidinyl]-butyl]-N''-methylguanidine

Obtained by operating as in Example 4 starting with 4.9 g (0.0176 moles) of 1-(4-aminobutyl)-4-(4-fluorobenzoyl)piperidine [prepared according to J. Vandenberk et al., European Patent No. 184,258; C.A. (1986) 105, 133907j] and with 2.05 g (0.0159 moles) of N-cyano-N'-methyl-S-methylisothiourea in 50 ml of 2-methoxyethanol. Heating time: 6 hours 30 min at 100° C. Chromatography eluent: methylene chloride/methanol 9/1. Yld: 2.2 g (38%), amorphous solid.

Percentage analysis C$_{19}$H$_{26}$FN$_5$O (FW = 359.45)

|            | C %   | H %  | F %  | N %   |
|------------|-------|------|------|-------|
| Calculated | 63.49 | 7.29 | 5.29 | 19.48 |
| Found      | 63.51 | 7.55 | 5.39 | 19.42 |

IR:
$\nu$ (C=O) = 1660 cm$^{-1}$
$\nu$ (C≡N) = 2140 cm$^{-1}$
N.M.R. (CDCl$_3$): δ = 0.8–3.6 (17H, m); 2.9 (3H, d is converted into s with D$_2$O); 5.8 (2H, peak exchangeable with D$_2$O); 6.9–7.3 (2H, m); 7.7–8.1 (2H, m).

EXAMPLE 15

N-Cyano-N'-[6-[4-(4-fluorobenzoyl)-1-piperidinyl]hexyl]-N''-methylguanidine (a)
[2-[6-[4-2-(4-Fluorophenyl)-1,3-dioxolan-2-yl]-1-piperidinyl]hexyl]-1H-isoindole-1,3(2H)-dione A mixture of 18.8 g (0.0748 moles) of 4-[(4-fluorophenyl)-1,3-dioxolan-2-yl]piperidine, of 25.6 g (0.0825 moles) of 2-(6-bromohexyl)-1H-isoindole-1,3(2H)dione [prepared according to E. F. Elslager et al., J. Am. Chem. Soc. (1957) 79, 4699] and of 11.4 g (0.0825 moles) of potassium carbonate in 150 ml of acetonitrile is heated under reflux for 3 hours. After removal of the suspended solid by filtration, the solution is concentrated to dryness under reduced pressure. The residue obtained is stirred in 500 ml of ethyl ether The suspension formed is filtered; the ethereal filtrate is evaporated down to yield 2-[6-[4-[2-(4-fluorophenyl)-1,3-dioxolan-2-yl]-1-piperidinyl]hexyl]-1H-isoindole-1,3(2H)dione. Yld: 31.0 g (86%), mp = 72°–76° C.

IR:
$\nu$ (C=O) = 1700 cm$^{-1}$
N.M.R. (CDCl$_3$): δ = 1.0–2.6 (17H, m); 2.7–3.2 (2H, m); 3.5–4.1 (6H, m); 6.7–8.0 (8H, m).

(b)
1-(6-Aminohexyl)-4-[2-(4-fluorophenyl)-1,3-dioxolan-2-yl]piperidine 3.6 g (0.0719 moles) of hydrazine hydrate are added dropwise at room temperature to a suspension of 30.5 g (0.0635 moles) of 2-[6-[4-[2-(4-fluorophenyl)-1,3-dioxolan-2-yl]-1-piperidinyl]hexyl]-1H-isoindole-1,3(2H)dione in 600 ml of ethanol. Stirring is continued for 23 hours at room temperature. Another 1.0 g (0.0200 moles) of hydrazine hydrate is then added and stirring is continued for another 16 hours. After a precipitate has been removed by filtration, the solution is concentrated under reduced pressure. The residue is taken up with water and extracted with methylene chloride. The combined organic extracts are dried over sodium sulfate and are concentrated to dryness under reduced pressure. The residue is used in the next stage without further purification. Yld: 19.0 g (85%).

N.M.R. (CDCl$_3$): δ = 0.9–4.1 (27H, m including 2H exchangeable with D$_2$O); 6.7–7.6 (4H, m).

(c) 1-(6-Aminohexyl)-4-(4-fluorobenzoyl)piperidine 75.0 g of 22% hydrochloric acid are added dropwise to a solution of 19.0 g (0.0542 moles) of 1-(6-aminohexyl)-4-[2-(4-fluorophenyl)-1,3-dioxolan-2-yl]piperidine in 140 ml of isopropanol. The mixture obtained is heated under reflux for 8 hours. After cooling, the reaction mixture is concentrated to dryness under reduced pressure. The residue, washed with ether and dried, yields 1-(6-aminohexyl)-4-(4-fluorobenzoyl)piperidine dihydrochloride. Yld: 18.6 g (90%), mp = 205°–208° C.

IR:
$\nu$ (C=O) = 1660 cm$^{-1}$
N.M.R. (DMSO-d$_6$): δ = 1.0–4.1 (23H, m including 2H exchangeable with CF$_3$COOD); 7.1–7.6 (2H, m); 7.7–8.3 (2H, m); 11.0 (2H, peak exchangeable with CF$_3$COOD). The base is obtained by taking up the dihydrochloride in dilute aqueous ammonia and extracting with methylene chloride. Yld: 15.0 g (quantitative).

IR:
$\nu$ (C=O) = 1660 cm$^{-1}$

N.M.R. (CDCl$_3$): δ=0.9–3.6 (23H, m including 2H exchangeable with D$_2$O); 6.8–7.3 (2H, m); 7.8–8.1 (2H, m).

(d)
N-Cyano-N'-[6-[4-(4-fluorobenzoyl)-1-piperidinyl]hexyl-N"-methylguanidine

Obtained by operating as in Example 4 starting with 6.0 g (0.0196 moles) of 1-(6-aminohexyl)-4-(4-fluorobenzoyl)piperidine and with 2.3 g (0.0178 moles) of N-cyano-N'-methyl-S-methylisothiourea in 50 ml of 2-methoxyethanol. Heating time: 2 hours at 85° C., then 7 hours 30 min at 115° C. Chromatography eluent: methylene chloride/methanol: 9/1. Yld: 1.2 g (17%), mp=121°–123° C.

Percentage analysis: C$_{21}$H$_{30}$FN$_5$O (FW=387.50)

|  | C % | H % | F % | N % |
|---|---|---|---|---|
| Calculated | 65.09 | 7.80 | 4.90 | 18.07 |
| Found | 65.03 | 7.95 | 4.86 | 17.95 |

IR:
ν (C=O)=1660 cm$^{-1}$
ν (C≡N)=2160 cm$^{-1}$

N.M.R. (CDCl$_3$): δ=0.8–2.7 (17H, m); 2.8 (3H, d is converted into s with D$_2$O); 2.8–3.5 (4H, m); 5.2 (1H, peak exchangeable with D$_2$O); 5.5 (1H, peak exchangeable with D$_2$O); 6.9–7.3 (2H, m); 7.7–8.1 (2H, m).

EXAMPLE 16

N,N'-Bis[2-[4-[4-fluorobenzoyl)-1-piperidinyl]ethyl]-N"-cyanoguanidine

A solution of 3.2 g (0.0127 moles) of 1-(2-aminoethyl)-4-(4-fluorobenzoyl)piperidine in 50 ml of ethanol is added dropwise to a suspension of 5.0 g (0.0127 moles) of N-cyano-N'-[2-[4-(4-fluorobenzoyl)-1-piperidinyl]ethyl]phenoxyformamidine in 60 ml of ethanol. The reaction mixture is stirred for 11 hours at room temperature and is then concentrated to dryness under reduced pressure. The residue is purified by chromatography on a silica column. Eluent: methylene chloride/methanol: 9/1. Evaporation of the eluate yields N,N'-bis[2-[4-(4-fluorobenzoyl)-1-piperidinyl]ethyl]-N'-cyanoguanidine. Yld: 1.1 g (16%), mp=152°–156° C. (ethanol).

Percentage analysis: C$_{30}$H$_{36}$F$_2$N$_6$O$_2$ (FW=550.65)

|  | C % | H % | F % | N % |
|---|---|---|---|---|
| Calculated | 65.44 | 6.59 | 6.90 | 15.26 |
| Found | 65.25 | 6.66 | 6.68 | 15.20 |

IR:
ν (C=O)=1655 cm$^{-1}$
ν (C≡N)=2160 cm$^{-1}$

N.M.R. (CDCl$_3$): 1.5–3.6 (26H, m); 6.7–7.3 (6H, m including 2H exchangeable with D$_2$O); 7.6–8.2 (4H, m).

EXAMPLE 17

N-Cyano-N'-[3-[4-(4-fluorobenzoyl)-1-piperidinyl]-2-hydroxy]propyl]-N"-methylguanidine (a)
1-Chloro-3-[4-[2-[4-fluorophenyl]-1,3-dioxolan-2-yl]-1-piperidinyl]propan-2-ol 20.4 g (0.220 moles) of epichlorohydrin are added dropwise to a suspension of 55.2 g (0.220 moles) of 4-[2-(4-fluorophenyl)-1,3-dioxolan-2-yl]piperidine in 220 ml of ethyl ether. Stirring is continued at room temperature for 12 hours after the end of the addition. The precipitate formed is isolated by filtration and dried. It is used in the next stage without further purification. Yld: 60.0 g (79%).

N.M.R. (CDCl$_3$+D$_2$O): 1.2–4.1 (18H, m); 6.7–7.5 (4H, m).

(b)
2-[3-[4-[2-(4-Fluorophenyl)-1,3-dioxolan-2-yl]-1-piperidinyl]-2-hydroxy]propyl]-1H-isoindole-1,3(2H)dione A mixture of 59.6 g (0.173 moles) of 1-chloro-3-[4-[2-(4-fluorophenyl)-1,3-dioxolan-2-yl]-1-piperidinyl]propan-2-ol and of 32.1 g (0.173 moles) of potassium phthalimide in 710 ml of N,N-dimethylformamide is heated under reflux for 2 hours. After coooling, the reaction mixture is thrown into 4.3 l of water. The suspension obtained is then stirred for 2 hours at room temperature. The precipitate is next isolated by filtration. It is washed with hexane and recrystallized from a mixture of hexane and ethyl acetate in the presence of Norit. Yld: 31.5 g (40%), mp=124°–126° C.

IR:
ν (C=O)=1690 cm$^{-1}$

N.M.R. (CDCl$_3$): δ=1.2–4.2 (18H, m); 6.7–7.5 (4H, m); 7.5–7.9 (4H, m).

(c)
1-Amino-3-[4-[2-(4-fluorophenyl)-1,3-dioxolan-2-yl-1-piperidinyl]propan-2-ol 3.9 g (0.0779 moles) of hydrazine hydrate are added dropwise at room temperature to a suspension of 31.5 g (0.0693 moles) of 2-[3-[4-[2-(4-fluorophenyl)-1,3-dioxolan-2-yl]-1-piperidinyl]-2-hydroxy]propyl]-1H-isoindole-1,3(2H)-dione in 650 ml of ethanol. Stirring is continued for 60 hours at room temperature. The solution obtained is concentrated under reduced pressure. The residue is taken up with 1 l of ethyl ether. The solid formed is isolated by filtration and washed with ether. It is next extracted with 3×500 ml of boiling chloroform. Concentration of these chloroform extracts yields 1-amino-3-[4-[2-(4-fluorophenyl)-1,3-dioxolan-2-yl]-1-piperidinyl]propan-2-ol, which is used in the next stage without other purification. Yld: 18.5 g (82%), mp=132°–136° C.

N.M.R. (CDCl$_3$): δ=1.3–4.1 (21H including 3H exchangeable with D$_2$O); 6.8–7.5 (4H, m).

(d)
1-Amino-3-[4-(4-fluorobenzoyl)-1-piperidinyl]propan-2-ol 44.1 g of 22% hydrochloric acid are added dropwise to a solution of 10.5 g (0.0324 moles) of 1-amino-3-[4-[2-(4-fluorophenyl)-1,3-dioxolan-2-yl]-1-piperidinyl]propan-2-ol in 85 ml of isopropanol. The mixture obtained is heated under reflux for 10 hours. After cooling, the reaction mixture is concentrated to dryness under reduced pressure. The residue, recrystallized from a mixture of ethanol and ethyl ether, yields 1-amino-3-[4-(4-fluorobenzoyl)-1-piperidinyl]propan-2-ol dihydrochloride. Yld: 9.2 g (80%), mp=189°–192° C.

Percentage analysis: C$_{15}$H$_{23}$Cl$_2$FN$_2$O$_2$ (FW=353.26)

|  | C % | H % | Cl | F % | N % |
|---|---|---|---|---|---|
| Calculated | 51.00 | 6.56 | 20.07 | 5.38 | 7.93 |

-continued

| | C % | H % | Cl | F % | N % |
|---|---|---|---|---|---|
| Found | 50.75 | 6.69 | 19.98 | 5.17 | 7.82 |

IR:
$\nu$ (C=O) = 1665 cm$^{-1}$

N.M.R. (DMSO-d$_6$30 CF$_3$COOD): $\delta$=1.7-2.2 (4H, m); 2.6-4.6 (10H, m); 7.0-7.4 (2H, m); 7.8-8.2 (2H, m). The base is obtained by taking up the dihydrochloride in dilute aqueous ammonia and extracting with methylene chloride. Yld: 6.9 g (95%), mp=89°-92° C.

IR:
$\nu$ (C=O) = 1655 cm$^{-1}$

N.M.R. (CDCl$_3$): $\delta$=1.6-4.0 (17H, m including 3H exchangeable with D$_2$O); 6.9-7.3 (2H, m); 7.7-8.1 (2H, m).

(e)
N-Cyano-N'-[3-[4-(4-fluorobenzoyl)-1-piperidinyl]-2-hydroxypropyl]-N"-methylguanidine A solution of 4.7 g (0.0168 moles) of 1-amino-3-[4-(4-fluorobenzoyl)-1-piperidinyl]propan-2-ol in 100 ml of ethanol is added dropwise at room temperature to a solution of 2.5 g (0.0168 moles) of dimethyl N-cyanodithioiminocarbonate in 100 ml of ethanol. The reaction mixture is stirred for 24 hours at room temperature. A release of methyl mercaptan is produced. 14.4 ml (0.116 moles) of a solution containing 33% methylamine in absolute ethanol is then added dropwise. The reaction mixture is stirred for 20 hours at room temperature. A new release of methyl mercaptan is produced. The solution obtained is concentrated to dryness under reduced pressure. The residue is purified by chromatography on a silica column. Eluent: methylene chloride/methanol: 9/1. Evaporation of the eluate yields N-cyano-N'-[3-[4-(4-fluorobenzoyl)-1-piperidinyl]-2-hydroxy]-propyl]-N"-methylguanidine. Yld: 3.4 g (28%), mp=141°-145° C. (ethyl acetate-ethanol).

Percentage analysis: C$_{18}$H$_{24}$FN$_5$O$_2$ (FW=361.42)

| | C % | H % | F % | N % |
|---|---|---|---|---|
| Calculated | 59.82 | 6.69 | 5.26 | 19.38 |
| Found | 59.64 | 6.53 | 5.35 | 19.60 |

IR:
$\nu$ (C=O) = 1660 cm$^{-1}$
$\nu$ (C≡N) = 2160 cm$^{-1}$

N.M.R. (CDCl$_3$): $\delta$=1.7-2.6 (8H, m); 2.9 (3H, d is converted into s with D$_2$O); 2.8-3.6 (5H,.m); 3.7-4.3 (2H, m including 1H exchangeable with D$_2$O); 6.2 (1H, peak exchangeable with D$_2$O); 6.9 (1H, peak exchangeable with D$_2$O); 6.9-7.4 (2H, m); 7.8-8.2 (2H, m).

EXAMPLE 18

N-Cyano-N'-[2-[4-(6-fluoro-1,2-benzisoxazol-3-yl)-1-piperidinyl]ethyl]-N"-methylguanidine (a)
6-Fluoro-3-[1-(2-phthalimidoethyl)-4-piperidinyl]-1,2-benzisoxazole A suspension of 20.0 g (0.091 moles) of 6-fluoro-3-(4-piperidinyl)-1,2-benzisoxazole [prepared according to J. T. Strupczewski et al., J. Med. Chem. (1985) 28, 761], of 23.0 g (0.091 moles) of N-(2-bromoethyl)phthalimide and of 12.6 g (0.091 moles) of potassium carbonate in 2.6 l of acetonitrile is heated under reflux for 4 hours. The reaction mixture is then filtered hot and the cake is washed with acetonitrile. The filtrate and the washing solution are combined and concentrated to dryness under reduced pressure. The residue obtained is taken up with water and extracted with methylene chloride. These organic extracts are washed with water, are dried over sodium sulfate and are concentrated to dryness under reduced pressure. The residue is purified by recrystallization from ethyl acetate in the presence of Norit. Yld: 13.7 g (38%), mp=143°-145° C.

Percentage analysis: C$_{22}$H$_{20}$FN$_3$O$_3$ (FW=393.42)

| | C % | H % | F % | N % |
|---|---|---|---|---|
| Calculated | 67.17 | 5.12 | 4.83 | 10.68 |
| Found | 67.03 | 5.30 | 4.93 | 10.60 |

IR:
$\nu$ (C=O) = 1690 cm$^{-1}$

N.M.R. (CDCl$_3$): $\delta$=1.7-3.5 (11H, m) including 2.7 (2H, t); 3.9 (2H, t); 6.7-8.1 (7H, m).

(b)
3-[1-(2-Aminoethyl)-4-piperidinyl]-6-fluoro-1,2-benzisoxazole 1.8 g (0.0360 moles) of hydrazine hydrate are added dropwise to a suspension of 12.3 g (0.0313 moles) of 6-fluoro-3-[1-(2-phthalimidoethyl)-4-piperidinyl]-1,2-benzisoxazole in 180 ml of ethanol. After 20 hours, stirring at room temperature, 45 ml of 10% potassium hydroxide are added to the reaction mixture and the ethanol is removed by concentration under reduced pressure. The residual aqueous solution is extracted with methylene chloride. The organic extracts are dried over sodium sulfate and concentrated to dryness under reduced pressure. The solid residue obtained is used in the next stage without other purification. Yld: 7.8 g (95%), mp=61°-65° C.

N.M.R. (CDCl$_3$): $\delta$=1.5-3.5 (15H, m) including 1.7 (2H, peak exchangeable with D$_2$O); 6.8-7.8 (3H, m).

(c)
N-Cyano-N'-[2-[4-(6-fluoro-1,2-benzisoxazol-3-yl)-1-piperidinyl]ethyl]-S-methylisothiourea Obtained by operating as in paragraph a of Example 1 starting with a solution of 2.1 g (0.0144 moles) of dimethyl N-cyanocarbonimidodithioate in 40 ml of ethanol and a solution of 4.0 g (0.0152 moles) of 3-[1-(2-aminoethyl)-4-piperidinyl]-6-fluoro-1,2-benzisoxazole in 40 ml of ethanol. Stirring time: 20 hours. Yld: 4.2 g (81%); mp=148°-151° C. (ethanol).

Percentage analysis: C$_{17}$H$_{20}$FN$_5$OS (FW=361.44)

| | C % | H % | F % | N % | S % |
|---|---|---|---|---|---|
| Calculated | 56.49 | 5.58 | 5.26 | 19.38 | 8.87 |
| Found | 56.78 | 5.57 | 5.38 | 19.35 | 9.00 |

IR:
$\nu$ (C≡N) = 2150 cm$^{-1}$

N.M.R. (CDCl$_3$): $\delta$=1.6-3.7 (16H, m) including 2.5 (3H, s) and 3.5 (2H, m is converted into t with D$_2$O); 6.6-7.4 (3H, m including 1H exchangeable with D$_2$O); 7.4-8.0 (1H, m).

(d) N-Cyano-N-[2-[4-(6-fluoro-1,2-benzisoxazol-3-yl)-1-piperidinyl]ethyl]-N''-methylguanidine 1.2 g (0.00332 moles) of N-cyano-N'-[2-[4-(6-fluoro-1,2-benzisoxazol-3-yl)-1-piperidinyl]ethyl]-S-methylisothiourea are added to 100 ml (0.803 moles) of a solution containing 33% methylamine in absolute ethanol. Stirring is continued for 20 hours at room temperature; a release of methyl mercaptan is produced. The solution obtained is then concentrated to dryness under reduced pressure. The residue is washed with ether and recrystallized from ethanol in the presence of Norit. Yld: 0.8 g (70%), mp=166°-168° C.

Percentage analysis: $C_{17}H_{21}FN_6O$ (FW=344.39)

|  | C % | H % | F % | N % |
|---|---|---|---|---|
| Calculated | 59.29 | 6.15 | 5.52 | 24.40 |
| Found | 59.27 | 6.25 | 5.21 | 24.27 |

IR:
$\nu$ (C≡N)=2150 cm$^{-1}$

N.M.R. (CDCl$_3$): δ=1.6–2.8 (8H, m); 2.8 (3H, d is converted into s with D$_2$O); 2.9–3.6 (5H, m); 6.0 (1H, peak exchangeable with D$_2$O); 6.8–8.0 (3H, m); 7.9 (1H, peak exchangeable with D$_2$O).

EXAMPLE 19

N-Cyano-N'-[3-[4-(6-fluoro-1,2-benzisoxazol-3-yl)-1piperidinyl]propyl]-N''-methylguanidine

(a)

6-Fluoro-3-[1-(3-phthalimidopropyl)-4-piperidinyl]-1,2-benzisoxazole

Obtained by operating as in paragraph a of Example 18 starting with 288.0 g (1.308 moles) of 6-fluoro-3-(4-piperidinyl)-1,2-benzisoxazole, with 350.6 g (1.308 moles) of N-(3-bromopropyl)phthalimide and with 180.6 g (1.307 moles) of potassium carbonate in 2.6 l of acetonitrile. Refluxing time: 5 hours 30 min. Yld: 357.7 g (67%), mp=128°-130° C. (ethyl acetate).

Percentage analysis: $C_{23}H_{22}FN_3O_2$ (FW=407.44)

|  | C % | H % | F % | N % |
|---|---|---|---|---|
| Calculated | 67.80 | 5.44 | 4.66 | 10.31 |
| Found | 67.60 | 5.42 | 4.73 | 10.30 |

IR:
$\nu$ (C=O)=1690 cm$^{-1}$

N.M.R. (CDCl$_3$): δ=1.6–3.3 (13H, m); 3.75 (2H, t); 6.7–7.3 (2H, m); 7.4–8.0 (5H, m).

(b)

3-[1-(3-Aminopropyl)-4-piperidinyl]-6-fluoro-1,2-benzisoxazole

Obtained by operating as in paragraph b of Example 18 starting with 46.6 g (0.931moles) of hydrazine hydrate and with 330.0 g (0.810 mole) of 6-fluoro-3-[1-(3-phthalimidopropyl)-4-piperidinyl]-1,2-benzisoxazole in 4.7 l of ethanol. Yld: 204.6 g (91%), mp=59°-62° C.

N.M.R. (CDCl$_3$): δ=1.4–3.6 (17H, m) including 1.8 (2H, peak exchangeable with D$_2$O); 6.8–7.4 (2H, m); 7.5–7.9 (1H, m).

(c)

N-Cyano-N'-[3-[4-(6-fluoro-1,2-benzisoxazol-3-yl)-1-piperidinyl]propyl]-N''-methylguanidine A solution of 130.2 g (0.469 moles) of 3-[1-(3-aminopropyl)-4-piperidinyl]-6-fluoro-1,2-benzisoxazole in 450 ml of ethanol is added dropwise to a solution of 64.5 g (0.441 moles) of dimethyl N-cyanocarbonimidodithioate in 1.2 l of ethanol. Stirring is continued for 22 hours at room temperature; a release of methyl mercaptan is produced. The reaction mixture is then treated by the addition of 520 ml (4.176 moles) of a solution containing 33% of methylamine in absolute ethanol and is heated to 60° C. for 3 hours. A new release of methyl mercaptan is produced. After cooling to about −10° C., the precipitate formed is isolated by filtration. Yld: 137.0 g (87%), mp=177°-180° C. (ethanol).

Percentage analysis: $C_{18}H_{23}FN_6O$ (FW=358.42)

|  | C % | H % | F % | N % |
|---|---|---|---|---|
| Calculated | 60.32 | 6.47 | 5.30 | 23.45 |
| Found | 60.23 | 6.77 | 5.48 | 23.26 |

IR:
$\nu$ (C≡N)=2150 cm$^{-1}$

N.M.R. (DMSO-d$_6$): δ=1.5–2.6 (10H, m); 2.7 (3H, d is converted into s with D$_2$O); 2.7–3.4 (5H, m); 7.0 (2H, peak exchangeable with D$_2$O); 6.9–8.1 (3H, m).

EXAMPLE 20

N-Cyano-N'-ethyl-N''-[3-[4-(6-fluoro-1,2-benzisoxazol-3-yl)-1-piperidinyl]propyl]guanidine

(a)

N-Cyano-N'-[3-[4-(6-fluoro-1,2-benzisoxazol-3-yl)-1-piperidinyl]propyl]1-S-methylisothiourea Obtained by operating as in paragraph a of Example 1 starting with a solution of 12.8 g (0.0875 moles) of dimethyl N-cyanocarbonimidodithioate in 240 ml of ethanol and with a solution of 25.8 g (0.0930 moles) of 3-[1-(3-aminopropyl)-4-piperidinyl]-6-fluoro-1,2-benzisoxazole in 240 ml of ethanol. Stirring time: 18 hours. Yld: 24.1 g (73%), mp=142°-145° C. (ethanol).

Percentage analysis: $C_{18}H_{22}FN_5OS$ (FW=375.47)

|  | C % | H % | F % | N % | S % |
|---|---|---|---|---|---|
| Calculated | 57.58 | 5.91 | 5.06 | 18.65 | 8.54 |
| Found | 57.42 | 6.08 | 5.38 | 18.62 | 8.27 |

IR:
$\nu$ (C≡N)=2160 cm$^{-1}$

N.M.R. (CDCl$_3$+D$_2$O): δ=1.6–3.3 (16H, m); 3.5 (2H, t); 6.8–7.4 (2H, m); 7.4–8.2 (1H, m).

(b)

N-Cyano-N'-ethyl-N''-[3-[4-(6-fluoro-1,2-benzisoxazol-3-yl)-1-piperidinyl]propyl]guanidine A mixture of 3.0 g (0.00799 moles) of N-cyano-N'-[3-[4-(6-fluoro-1,2-benzisoxazol-3-yl)-1-piperidinyl]propyl]-S-methylisothiourea and of 25 ml (0.377 moles) of ethylamine is stirred for 3 hours at room temperature. A release of methyl mercaptan is produced. When the ethylamine has evaporated off, the same quantity of it as before is added again and stirring is continued for 1 hour. After evaporation of the ethylamine, the residue is recrystallized from ethanol. Yld: 2.6 g (87%), mp=153°-155° C.

Percentage analysis: $C_{19}H_{25}FN_6O$ (FW=372.45)

|  | C % | H % | F % | N % |
|---|---|---|---|---|
| Calculated | 61.27 | 6.77 | 5.10 | 22.56 |
| Found | 61.16 | 6.79 | 5.16 | 22.65 |

IR:

$\nu$ (C≡N)=2150 cm$^{-1}$

N.M.R. (DMSO-d$_6$): δ=1.1 (3H, t); 1.4–2.5 (10H, m); 2.7–3.5 (7H, m); 6.7–8.2 (5H, m including 2H exchangeable with D$_2$O).

EXAMPLE 21

N'-Cyano-N,N-dimethyl-N''-[3-[4-(6-fluoro-1,2-benzisoxazol-3-yl)-1-piperidinyl]propyl]guanidine Obtained by operating as in Example 4, starting with 5.8 g (0.0209 moles) of 3-[1-(3-aminopropyl)-4-piperidinyl]-6-fluoro-1,2-benzisoxazole and with 3.0 g (0.0209 moles) of N'-cyano-N,N-dimethyl-S-methylisothiourea in 70 ml of ethanol. Refluxing time: 9 hours 30 min. Chromatography eluent: methylene chloride/methanol: 95/5. Yld: 3.8 g (49%), mp=108°-111° C.

Percentage analysis: $C_{19}H_{25}FN_6O$ (FW=372.45)

|  | C % | H % | F % | N % |
|---|---|---|---|---|
| Calculated | 61.27 | 6.77 | 5.10 | 22.56 |
| Found | 61.24 | 6.97 | 5.10 | 22.57 |

IR:

$\nu$ (C≡N)=2140 cm$^{-1}$

N.M.R. (CDCl$_3$): δ=1.6–3.3 (19H, m) including 3.0 (6H, s); 3.4–3.9 (2H, m is converted into t with D$_2$O); 6.7–7.4 (3H, m including 1H exchangeable with D$_2$O); 7.4–7.9 (1H, m).

EXAMPLE 22

N-Cyano-N'-[3-[4-(6-fluoro-1,2-benzisoxazol-3-yl)-1-piperidinyl]propyl]guanidine A solution of 1.5 g (0.00541 moles) of 3-[1-(3-aminopropyl)-4-piperidinyl]-6-fluoro-1,2-benzisoxazole and of 0.6 g (0.00521 moles) of N-cyano-S-methylisothiourea in 50 ml of ethanol is heated under reflux for 8 hours. After cooling to about −10° C., the precipitate formed is isolated by filtration. It is purified by chromatography on a silica column (eluent: methylene chloride/methanol: 95/5) and then by recrystallization from ethanol. Yld: 0.5 g (28%), mp=178°-181° C.

Percentage analysis: $C_{17}H_{21}FN_6O$ (FW=344.39)

|  | C % | H % | F % | N % |
|---|---|---|---|---|
| Calculated | 59.29 | 6.15 | 5.52 | 24.40 |
| Found | 59.01 | 6.51 | 5.71 | 24.70 |

IR:

$\nu$ (C≡N)=2155 cm$^{-1}$

N.M.R. (DMSO-d$_6$): δ=1.3–3.5 (15H, m); 6.7 (3H, broadened peak exchangeable with CF$_3$COOD); 6.9–8.2 (3H, m)

EXAMPLE 23

N-Cyano-N'-(3,3-dimethyl-2-butyl)-N''-[3-[4-(6-fluoro-1,2-benzisoxazol-3-yl)-1-piperidinyl]propyl]guanidine (a)

N-Cyano-N'-(3,3-dimethyl-2-butyl)-S-methylisothiourea

A solution of 2.0 g (0.0137 moles) of dimethyl N-cyanodithioiminocarbonate and of 1.4 g (0.0138 moles) of 2-amino-3,3-dimethylbutane in 50 ml of ethanol is stirred for 3 days at room temperature. A release of methyl mercaptan is produced. After cooling to about −10° C., the precipitate formed is isolated by filtration. Yld: 1.6 g (59%), mp=143°-146° C. (ethanol).

Percentage analysis: $C_9H_{17}N_3S$ (FW=199.32)

|  | C % | H % | N % | S % |
|---|---|---|---|---|
| Calculated | 54.23 | 8.60 | 21.08 | 16.09 |
| Found | 54.27 | 8.64 | 21.02 | 16.18 |

IR:

$\nu$ (C≡N)=2150 cm$^{-1}$

N.M.R. (CDCl$_3$): δ=0.9 (9H, s); 1.2 (3H, d); 2.5 (3H, s); 3.7 (1H, m), 5.9 (1H, broadened peak exchangeable with D$_2$O).

(b)

N-Cyano-N'-(3,3-dimethyl-2-butyl)-N''-3-[4-(6-fluoro-1,2-benzisoxazol-3-yl)-1-piperidinyl]propyl]guanidine Obtained by operating as in Example 4 starting with 1.2 g (0.00433 moles) of 3-[1-(3-aminopropyl)-4-piperidinyl]-6-fluoro-1,2-benzisoxazole and with 0.8 g (0.00401 moles) of N-cyano-N'-(3,3-dimethyl-2-butyl)-S-methylisothiourea in 50 ml of 2-methoxyethanol. Refluxing time: 10 hours. Chromatography eluent:methylene chloride/methanol: 95/5. Yld: 0.7 g (41%), mp=164°-166° C. (ethanol).

Percentage analysis: $C_{23}H_{33}FN_6O$ (FW=428.56)

|  | C% | H% | F% | N% |
|---|---|---|---|---|
| Calculated | 64.46 | 7.76 | 4.43 | 19.61 |
| Found | 64.65 | 7.74 | 4.35 | 19.39 |

IR:

$\nu$ (C≡N)=2150 cm$^{-1}$

N.M.R. (CDCl$_3$): δ=1.0 (9H, s); 1.2 (3H, d); 1.3–4.0 (15H, m); 4.7–5.4 (1H, m), 6.7–7.4 (4H, m including 2H exchangeable by D$_2$O); 7.6–8.0 (1H, m).

EXAMPLE 24

N-[2-[4-(4-Fluorobenzoyl)-1-piperidinyl]ethyl]-N'-methyl-2-nitro-1,1-ethenediamine (a) N-[2-[4-(4-Fluorobenzoyl)-1-piperidinyl]ethyl]-1-(methylthio)-2-nitroethenamine A suspension of 11.0 g (0.044 moles) of 1-(2-aminoethyl)-4-(4-fluorobenzoyl)piperidine and of 7.3 g (0.044 moles) of 1,1-bis(methylthio)-2-nitroethylene in 100 ml of acetonitrile is heated under reflux for 7 hours. A release of methyl mercaptan is produced. After cooling, the solution obtained is concentrated to dryness under reduced pressure. The residue is made concrete in iced ethyl acetate and recrystallized from isopropanol. Yld: 7.4 g (46%), mp=106°-110° C. An analytical sample was prepared by chromatography on a silica column.

Eluent: methylene chloride/methanol: 98/2. Mp=123°-125° C. (ethanol).

Percentage analysis: C₁₇H₂₂FN₃O₃S (FW=367.44)

|  | C% | H% | F% | N% | S% |
|---|---|---|---|---|---|
| Calculated | 55.57 | 6.04 | 5.17 | 11.44 | 8.73 |
| Found | 55.42 | 6.03 | 5.05 | 11.34 | 8.66 |

IR:
ν (C=O)=1655 cm⁻¹
N.M.R. (CDCl₃): δ=1.6-3.3 (11H, m); 2.4 (3H, s); 3.5 (2H, q is converted into t with D₂O); 6.5 (1H, s); 6.9-7.3 (2H, m); 7.8-8.1 (2H, m); 10.6 (1H, peak exchangeable with D₂O).

(b)
N-[2-[4-(4-Fluorobenzoyl)-1-piperidinyl]1ethyl]-N'-methyl-2-nitro-1,1-ethenediamine 6.4 g (0.0174 moles) of N-[2-[4-(4-fluorobenzoyl)-1-piperidinyl]ethyl]-1-(methylthio)-2-nitroethenamine are added to 18 ml (0.145 moles) of a solution containing 33% of methylamine in absolute ethanol. The solution obtained is made lukewarm very gradually. At 30° C., an abundant precipitate appears, accompanied by a considerable release of methyl mercaptan. Stirring is then continued for 2 hours at room temperature. The precipitate formed i isolated by filtration. It is washed with isopropyl ether and recrystallized from ethanol in the presence of Norit. Yld: 3.6 g (59%), mp=157°-159° C.

Percentage analysis: C₁₇H₂₃FN₄O₃ (FW=350.39)

|  | C% | H% | F% | N% |
|---|---|---|---|---|
| Calculated | 58.27 | 6.62 | 5.42 | 15.99 |
| Found | 58.39 | 6.66 | 5.35 | 16.09 |

IR:
ν (C=O)=1660 cm⁻¹
N.M.R. (CDCl₃) 1.5-3.6 (13H, m); 2.8 (3H, d is converted into s with D₂O); 6.5 (1H, s); 6.8-7.3 (2H, m); 7.7-8.2 (2H, m); 9.4 (1H, peak exchangeable with D₂O); 10.2 (1H, peak exchangeable with D₂O).

EXAMPLE 25

N-[3-[4-(4-Fluorobenzoyl)-1-piperidinyl]propyl]-N'-methyl-2-nitro-1,1-ethenediamine (a)
N-3-[4-(4-Fluorobenzoyl)-1-piperidinyl]propyl]-1-(methylthio)-2-nitroethenamine A mixture of 6.0 g (0.0227 moles) of 1-(3-aminopropyl)-4-(4-fluorobenzoyl)piperidine and of 3.1 g (0.0188 moles) of 1,1-bis(methylthio)-2-nitroethylene in ml of acetonitrile is heated under reflux for 6 hours. A release of methyl mercaptan is produced. After cooling, the solution obtained is concentrated to dryness under reduced pressure. The oily residue is purified by chromatography on a silica column. Eluent: methylene chloride/methanol: 95/5. Yld: 1.9 g (26%), mp=92°-94° C. (ethanol).

Percentage analysis: C₁₈H₂₄FN₃O₃S (FW=381.47)

|  | C% | H% | F% | N% | S% |
|---|---|---|---|---|---|
| Calculated | 56.68 | 6.34 | 4.98 | 11.02 | 8.40 |

-continued

|  | C% | H% | F% | N% | S% |
|---|---|---|---|---|---|
| Found | 56.45 | 6.47 | 4.85 | 10.83 | 8.70 |

IR:
ν (C=O)=1660 cm⁻¹
N.M.R. (CDCl₃): δ=1.5-3.8 (18H, m) including 2.4 (3H, s) and 3.5 (2H, q is converted into t with D₂O); 6.5 (1H, s); 6.9-7.3 (2H, m); 7.8-8.2 (2H, m); 10.6 (1H, peak exchangeable with D₂O).

(b)
N-3-[4-(4-Fluorobenzoyl)-1-piperidinyl]propyl]-N'-methyl-2-nitro-1,1-ethenediamine A mixture of 1.7 g (0.00446 moles) of N-[3-[4-(4-fluorobenzoyl)-1-piperidinyl]propyl]-1-(methylthio)-2-nitroethenamine and of 20 ml (0.161 moles) of a solution containing 33% of methylamine in absolute ethanol is stirred for 6 hours at room temperature. After two days at rest, the reaction mixture is filtered. The cake is washed with ether and purified by chromatography on a silica column. Eluent: methylene chloride/methanol: 95/5. Yld: 1.0 g (62%), mp=160°-162° C.

Percentage analysis: C₁₈H₂₅FN₄O₃ (FW=364.42)

|  | C% | H% | F% | N% |
|---|---|---|---|---|
| Calculated | 59.33 | 6.92 | 5.21 | 15.37 |
| Found | 59.32 | 7.03 | 5.33 | 15.56 |

IR:
ν (C=O)=1655 cm⁻¹
N.M.R. (CDCl₃): δ=1.5-3.7 (18H, m); 6.6 (1H, s); 6.9-7.4 (2H, m); 7.6 (1H, peak exchangeable with D₂O); 7.8-8.2 (2H, m); 10.2 (1H, peak exchangeable with D₂O).

EXAMPLE 26

N-[2-[4-(6-Fluoro-1,2-benzisoxazol-3-yl)-1-piperidinyl]ethyl]-N'-methyl-2-nitro-1,1-ethenediamine (a)
N-[2-[4-(6-Fluoro-1,2-benzisoxazol-3-yl)-1-piperidinyl]ethyl]-1-(methylthio)-2-nitroethenamine Obtained by operating as in paragraph a of Example 25 starting with 3.7 g (0.0141 moles) of 3-[1-(2-aminoethyl)-4-piperidinyl]-6-fluoro-1,2-benzisoxazole and with 2.2 g (0.0133 moles) of 1,1-bis(methylthio)-2-nitroethylene in 55 ml of acetonitrile. Reflux time: 3 hours 30 min. Chromatography eluent: methylene chloride/methanol: 98/2. Yld: 1.3 g (26%), mp=150°-154° C.

Percentage analysis: C₁₇H₂₁FN₄O₃S (FW=380.44)

|  | C% | H% | F% | N% | S% |
|---|---|---|---|---|---|
| Calculated | 53.67 | 5.56 | 4.99 | 14.73 | 8.43 |
| Found | 53.61 | 5.73 | 4.93 | 14.39 | 8.41 |

N.M.R. (CDCl₃): δ=1.8-3.3 (14H, m) including 2.4 (3H, s) and 2.7 (2H, t); 3.5 (2H, q is converted into t with D₂O); 6.5 (1H, s); 6.8-7.3 (2H, m); 7.6-8.0 (1H, m); 10.8 (1H, peak exchangeable with D₂O).

(b) N-[2-[4-(6-Fluoro-1,2-benzisoxazol-3-yl)-1-piperidinyl]ethyl]-N'-methyl-2-nitro-1,1-ethenediamine A mixture of 1.0 g (0.00263 moles) of N-[2-[4-(6-fluoro-1,2-benzisoxazol-3-yl)-1-piperidinyl]ethyl]-1-(methylthio)-2-nitroethenamine and of 75 ml of a solution containing 33% of methylamine in absolute ethanol is stirred for 48 hours at room temperature. A release of methyl mercaptan is produced. After cooling to about −10° C., the precipitate formed is isolated by filtration; it is washed with ether and recrystallized from ethanol. Yld: 0.7 g (73%), mp=181°–182.5° C.

Percentage analysis: $C_{17}H_{22}FN_5O_3$ (FW=363.39)

|  | C% | H% | F% | N% |
|---|---|---|---|---|
| Calculated | 56.19 | 6.10 | 5.23 | 19.27 |
| Found | 56.44 | 5.97 | 5.51 | 19.26 |

N.M.R. (CDCl$_3$): δ=1.5–3.7 (16H, m) including 2.8 (3H, s after exchange with D$_2$O); 6.5 (1H, s); 6.8–7.4 (2H, m); 7.4–7.8 (1H, m); 9.1 (1H, peak exchangeable with D$_2$O); 10.2 (1H, peak exchangeable with D$_2$O).

EXAMPLE 27

N-Cyano-N'-[2-[4-[2-(4-fluorophenyl)-1,3-dioxolan-2-yl]-1-piperidinyl]ethyl]piperidinoformamidine Obtained by operating as in Example 3 starting with 2.0 g (0.068 moles) of 1-(2-aminoethyl)-4-[2-(4-fluorophenyl)-1,3-dioxolan-2-yl]piperidine and with 1.25 g (0.068 moles) of N-cyano-S-methylpiperidinothioformamide [prepared according to R. Neidlein and U. Askani, Arch. Pharm. (Weinheim) (1977) 310, 820] in 40 ml of ethanol. Refluxing time: 34 hours. Yld: 1.0 g (34%), mp=155°–157° C. (ethanol-ethyl ether).

Percentage analysis: $C_{23}H_{32}FN_5O_2$ (FW=429.54)

|  | C% | H% | F% | N% |
|---|---|---|---|---|
| Calculated | 64.31 | 7.51 | 4.42 | 16.30 |
| Found | 64.07 | 7.47 | 4.32 | 16.03 |

IR:
$\nu$ (C≡N)=2150 cm$^{-1}$
N.M.R. (CDCl$_3$): δ=1.3–3.6 (23H, m); 3.5–4.1 (4H, m); 5.6–5.9 (1H, m exchangeable with CF$_3$COOD); 6.7–7.5 (4H, m).

EXAMPLE 28

N-Cyano-N'-[2-[4-(4-fluorobenzoyl)-1-piperidinyl]ethyl]piperidinoformamidine

Obtained by operating as in Example 4 starting with 5.0 g (0.020 moles) of 1-(2-aminoethyl)-4-(4-fluorobenzoyl)piperidine and with 3.7 g (0.020 moles) of N-cyano-S-methylpiperidinothioformamide in 50 ml of ethanol. Refluxing time: 13 hours. Chromatography eluent: methylene chloride/methanol: 98/2. Yld: 1.6 g (21%), mp=139°–141° C. (ethanol - isopropyl ether).

Percentage analysis: $C_{21}H_{28}FN_5O$ (FW=385.48)

|  | C% | H% | F% | N% |
|---|---|---|---|---|
| Calculated | 65.43 | 7.32 | 4.93 | 18.17 |
| Found | 65.33 | 7.32 | 4.87 | 18.19 |

IR:
$\nu$ (C=O)=1670 cm$^{-1}$
$\nu$ (C≡N)=2150 cm$^{-1}$
N.M.R. (CDCl$_3$): δ=1.4–3.8 (23H, m); 5.7 (1H, peak exchangeable with D$_2$O), 6.9–7.4 (2H, m), 7.8–8.2 (2H, m).

EXAMPLE 29

N-Cyano-N'-methyl-[4-(4-fluorobenzoyl)-1-piperidinyl]formamidine (a)

N-Cyano-S-methyl-[4-(4-fluorobenzoyl)-1-piperidinyl]thioformamide

A solution of 3.0 g (0.0145 moles) of 4-(4-fluorobenzoyl)piperidine in 30 ml of ethanol is added dropwise to a solution of 2.1 g (0.0145 moles) of dimethyl N-cyanocarbonimidodithioate in 50 ml of ethanol. Stirring is continued for 7 hours at room temperature. A release of methyl mercaptan is produced. The solution obtained is next concentrated to dryness under reduced pressure. The residue is washed with isopropyl ether and recrystallized from a mixture of ethanol and isopropyl ether. Yld: 2.5 g (56%), mp=101°–103° C. (ethanol).

IR:
$\nu$ (C=O)=1670 cm$^{-1}$
$\nu$ (C≡N)=2160 cm$^{-1}$
N.M.R. (CDCl$_3$): δ=1.7–2.2 (4H, m); 2.8 (3H, s); 3.1–3.8 (3H, m); 4.3–4.8 (2H, m); 7.0–7.4 (2H, m), 7.8–8.2 (2H, m).

(b)

N-Cyano-N'-methyl-[4-(4-fluorobenzoyl)-1-piperidinyl]thioformamidine 16 ml (0.129 moles) of a solution containing 33% of methylamine in absolute ethanol are added dropwise to a suspension of 2.4 g (0.0079 moles) of N-cyano-S-methyl-[4-(4-fluorobenzoyl)-1-piperidinyl]thioformamide in 50 ml of ethanol. The solution obtained is stirred for 5 hours at room temperature. A release of methyl mercaptan is produced. The reaction mixture is next concentrated to dryness under reduced pressure. The residue is washed with isopropyl ether and recrystallized from a mixture of methanol and isopropyl ether in the presence of Norit. Yld: 1.3 g (57%), mp=128°–130° C.

Percentage analysis: $C_{15}H_{17}FN_4O$ (FW=288.33)

|  | C% | H% | F% | N% |
|---|---|---|---|---|
| Calculated | 62.49 | 5.94 | 6.59 | 19.43 |
| Found | 62.42 | 6.01 | 6.85 | 19.58 |

IR:
$\nu$ (C=O)=1665 cm$^{-1}$
$\nu$ (C≡N)=2150 cm$^{-1}$
N.M.R. (CDCl$_3$): δ=1.6–2.1 (4H, m); 2.9–3.8 (3H, m); 3.0 (3H, d is converted into s with CF$_3$COOD); 3.8–4.3 (2H, m); 5.6–6.1 (1H, m exchangeable with CF$_3$COOD); 6.9–7.4 (2H, m); 7.7–8.2 (2H, m).

EXAMPLE 30

N-Cyano-N'-[2-[4-(4-fluorobenzoyl)-1-piperidinyl]ethyl]-4-(4-fluorobenzoyl)-1-piperidinyl]formamidine Obtained by operating as in Example 4 starting with 5.0 g (0.020 moles) of 1-(2-aminoethyl)-4-(4-fluorobenzoyl)piperidine and with 3.6 g (0.012 moles) of N-cyano-S-methyl-[4-(4-fluorobenzoyl)-1-piperidinyl]thioformamide in 100 ml of ethanol. Refluxing time: 21 hours 30 min. Chromatography eluent: methylene chloride/methanol: 95/5. Yld: 1.1 g (18%), mp=137°–139° C. (ethanol - isopropyl ether).

Percentage analysis: $C_{28}H_{31}F_2N_5O_2$ (FW=507.58)

| | C% | H% | F% | N% |
|---|---|---|---|---|
| Calculated | 66.26 | 6.16 | 7.49 | 13.80 |
| Found | 65.99 | 6.22 | 7.44 | 13.71 |

IR:
$\nu$ (C=O) = 1665 cm$^{-1}$
$\nu$ (C≡N) = 2150 cm$^{-1}$

N.M.R. (CDCl$_3$): $\delta$ = 1.5–4.4 (22H, m); 5.9 (1H, peak exchangeable with D$_2$O); 6.9–7.4 (4H, m); 7.7–8.2 (4H, m).

EXAMPLE 31

N-Cyano-N'-methyl-[4-(6-fluoro-1,2-benzisoxazol-3-yl)-1-piperidinyl]formamidine (a)

N-Cyano-S-methyl-[4-(6-fluoro-1,2-benzisoxazol-3-yl)-1-piperidinyl]thioformamide A suspension of 4.0 g (0.0182 moles) of 6-fluoro-3-(4-piperidinyl)-1,2-benzisoxazole in 30 ml of ethanol is added dropwise to a solution of 2.4 g (0.0164 moles) of dimethyl N-cyanocarbonimidodithioate in 40 ml of ethanol. Stirring is continued for 2 hours at room temperature. A release of methyl mercaptan is produced. The reaction mixture is next heated to 60° C. for 1 hour; after cooling, it is concentrated to dryness under reduced pressure. The residue is recrystallized from ethanol in the presence of Norit. Yld: 3.1 g (59%); mp=48°–151° C.

Percentage analysis: C$_{15}$H$_{15}$FN$_4$OS (FW=318.37)

| | C% | H% | F% | N% | S% |
|---|---|---|---|---|---|
| Calculated | 56.59 | 4.75 | 5.97 | 17.60 | 10.07 |
| Found | 56.36 | 4.88 | 6.13 | 17.37 | 9.77 |

IR:
$\nu$ (C≡N) = 2160 cm$^{-1}$

N.M.R. (CDCl$_3$): $\delta$ = 1.6–2.5 (4H, m); 2.8 (3H, s); 3.2–3.8 (3H, m); 4.3–4.9 (2H, m); 6.8–7.9 (3H, m).

(b)

N-Cyano-N'-methyl-[4-(6-fluoro-1,2-benzisoxazol-3-yl)-1-piperidinyl]formamidine 5.1 ml (0.0410 moles) of a solution containing 3% of methylamine in absolute ethanol are added to a suspension of 1.6 g (0.00503 moles) of N-cyano-S-methyl-[4-(6-fluoro-1,2-benzisoxazol-3-yl)-1-piperidinyl]thioformamide in 30 ml of ethanol. Stirring is continued for 16 hours at room temperature; a release of methyl mercaptan is produced. The same quantity of methylamine solution as before is then added again and stirring is continued for another 8 hours. After cooling to about −10° C., the precipitate formed is isolated by filtration; it is washed with ether and dried. Yld: 1.3 g (86%), mp=164°–167° C. (ethanol).

Percentage analysis: C$_{15}$H$_{16}$FN$_5$O (FW=301.32)

| | C% | H% | F% | N% |
|---|---|---|---|---|
| Calculated | 59.79 | 5.35 | 6.30 | 23.24 |
| Found | 59.61 | 5.47 | 6.39 | 23.20 |

IR:
$\nu$ (C≡N) = 2150 cm$^{-1}$

N.M.R. (DMSO-d$_6$): $\delta$ = 1.5–2.3 (4H, m); 2.9 (3H, d is converted into s with CF$_3$COOD); 3.0–4.4 (5H, m); 7.0–8.2 (4H, m including 1H exchangeable with CF$_3$COOD).

EXAMPLE 32

N-Carbamoyl-N'-[2-[4-(4-fluorobenzoyl)-1-piperidinyl]ethyl]-N''-methylguanidine dimaleate A solution of 3.0 g (0.0080 moles) of N-cyano-N'-[2-[4-[2-(4-fluorophenyl)-1,3-dioxolan-2-yl]-1-piperidinyl]ethyl]-N''-methylguanidine in 69 ml of 1 N hydrochloric acid is brought to reflux over 15 minutes and kept thus for 2 minutes. After rapid cooling using a water bath, the reaction mixture is made basic using 30% sodium hydroxide and is then extracted with methylene chloride. The combined organic extracts are washed with a saturated aqueous solution of sodium chloride, are dried over sodium sulfate and are concentrated to dryness under reduced pressure. The residue is dissolved in 100 ml of ethanol and a solution of 2.1 g (0.018 moles) of maleic acid in 50 ml of ethanol is added. The solution thus formed is concentrated to dryness under reduced pressure. The residue is purified by recrystallization from ethanol. Yld: 3.0 g (64%); mp=148°–150° C. (decomposition).

Percentage analysis: C$_{25}$H$_{32}$FN$_5$O$_{10}$ (FW=581.55)

| | C% | H% | F% | N% |
|---|---|---|---|---|
| Calculated | 51.63 | 5.55 | 3.27 | 12.04 |
| Found | 51.84 | 5.72 | 3.27 | 12.04 |

IR:
$\nu$ (C=O) = 1665 cm$^{-1}$

N.M.R. (DMSO-d$_6$30 CF$_3$COOD): $\delta$ = 2.9 (3H, s); 1.4–4.0 (13H, m); 6.2 (4H, s); 7.0–7.5 (2H, m); 7.8–8.2 (2H, m).

EXAMPLE 33

N-Carbamoyl-N'-[3-[4-(4-fluorobenzoyl)-1-piperidinyl]propyl]-N''-methylguanidine dimaleate Obtained by operating as in Example 32 starting with 2.0 g (0.0051 moles) of N-cyano-N'-[3-[4-[2-(4-fluorophenyl)-1,3-dioxolan-2-yl]-1-piperidinyl]propyl]-N''-methylguanidine and with 44 ml of 1 N hydrochloric acid and subsequent addition of a solution of 1.2 g (0.010 moles) of maleic acid in 50 ml of ethanol. Yld: 1.8 g (59%), mp=149°–151° C. (decomposition) (ethanol).

Percentage analysis: C$_{26}$H$_{34}$FN$_5$O$_{10}$ (FW=595.58)

| | C% | H% | F% | N% |
|---|---|---|---|---|
| Calculated | 52.43 | 5.75 | 3.19 | 11.76 |
| Found | 52.53 | 5.76 | 3.12 | 11.50 |

(C=O) = 1660 cm$^{-1}$

N.M.R. (DMSO-d$_6$+CF$_3$COOD): $\delta$ = 2.8 (3H, s); 1.5–4.0 (15H, m); 6.2 (4H, s); 7.0–7.5 (2H, m); 7.8–8.2 (2H, m).

EXAMPLE 34

N-Carbamoyl-N'-[3-[4-(6-fluoro-1,2-benzisoxazol-3-yl)-1-piperidinyl]propyl]-N''-methylguanidine dimaleate Obtained by operating as in Example 32 starting with 2.0 g (0.00558 moles) of N-cyano-N'-[3-[4-(4-fluoro-benzoyl)-1-piperidinyl]propyl]-N''-methylguanidine and with 47 ml of 1 N hydrochloric acid and subsequent addition of a solution of 0.86 g (0.00741 moles) of maleic acid in 50 ml of ethanol. Yld: 1.5 g (44%), mp=136° C. (decomposition) (ethanol).

Percentage analysis: $C_{26}H_{33}FN_6O_{10}$ (FW=608.58)

|  | C% | H% | F% | N% |
|---|---|---|---|---|
| Calculated | 51.31 | 5.47 | 3.12 | 13.81 |
| Found | 51.66 | 5.52 | 2.86 | 13.55 |

N.M.R. (DMSO-$d_6$+CF$_3$COOD): δ=1.5–4.0 (18H, m) including 2.9 (3H, s); 6.2 (4H, s); 7.0–8.1 (3H, m).

EXAMPLE 35

N-Cyano-N'-[3-[4-(6-fluoro-1,2-benzisoxazol-3-yl)-1-piperidinyl]propyl]1-N'''-methylguanidine (a)

3-[4-(6-Fluoro-1,2-benzisoxazol-3-yl)-1-piperidinyl]propionamide

A solution of 3.4 g (0.0156 moles) of 6-fluoro-3-(4-piperidinyl)-1,2-benzisoxazole and of 1.3 g (0.0187 moles) of acrylamide in 25 ml of ethanol is heated under reflux for 5 hours. The reaction mixture is then cooled to 0° C. The precipitate formed is isolated by filtration, washed with ether and dried. Yld: 3.8 g (84%), mp=144°–147° C.

IR:

ν (C=O)=1650 cm$^{-1}$

N.M.R. (CDCl$_3$): δ=1.8–3.3 (13H, m); 5.8 (1H, peak exchangeable with D$_2$O); 6.8–7.7 (3H, m); 7.8 (1H, peak exchangeable with D$_2$O).

(b) 3-[1-(3-Aminopropyl)-4-piperidinyl]-6-fluoro-1,2-benzisoxazole 3.8 g (0.013 moles) of 3-[4-(6-fluoro-1,2-benzisoxazol-3-yl)-1-piperidinyl]propionamide in suspension in 50 ml of tetrahydrofuran are added portionwise to a suspension of 1.9 g (0.050 moles) of lithium aluminium hydride in 100 ml of tetrahydrofuran. The reaction mixture is stirred under nitrogen atmosphere for 20 hours. After cooling to about 10° C., the excess metal hydride is destroyed by adding 15 ml of ethyl acetate and then 15 ml of 10% sodium hydroxide. The hydroxides formed are filtered off and washed with methylene chloride. The filtrate and the wash solutions are combined, washed with brine and dried over sodium sulfate and concentrated to dryness under reduced pressure. The residue is used in the next stage without other purification. It is identical with the product obtained in paragraph b of Example 19. Yld: 3.6 g (quantitative).

(c)

N-Cyano-N'-[3-[4-(6-fluoro-1,2-benzisoxazol-3-yl)-1-piperidinyl]propyl]-S-methylisothiourea A solution of 3.6 g (0.013 moles) of 3-[1-(3-aminopropyl)-4-piperidinyl]-6-fluoro-1,2-benzisoxazole in 90 ml of ethanol is added dropwise to a solution of 1.5 g (0.0103 moles) of dimethyl N-cyanocarbonimidodithioate in 90 ml of ethanol. The mixture is stirred for 24 hours at room temperature. A release of methyl mercaptan is produced. The solution obtained is concentrated to dryness under reduced pressure. The residue is purified by chromatography on a silica column. Eluent: methylene chloride/methanol: 95/5. Evaporation of the eluate yields a product identical with that obtained in paragraph a of Example 20. Yld: 1.3 g (27%).

(d)

N-Cyano-N'-[3-[4-(6-fluoro-1,2-benzisoxazol-3-yl)-1piperidinyl]propyl]-N'''-methylguanidine A solution of 1.3 g (0.0035 moles) of N-cyano-N'-[3-[4-(6-fluoro-1,2-benzisoxazol-3-yl)-1-piperidinyl]-propyl]-S-methylisothiourea in 100 ml of a solution containing 33% of methylamine in absolute ethanol is stirred at room temperature for 20 hours. A release of methyl mercaptan is produced. The solution obtained is next concentrated to a volume of approximately 30 ml and cooled to about −20° C. The precipitate formed is isolated by filtration; it is washed with ether and recrystallized from ethanol. It is identical with the product obtained in paragraph c of Example 19. Yld: 0.8 g (64%).

Percentage analysis: $C_{18}H_{23}FN_6O$ (FW=358.42)

|  | C% | H% | F% | N% |
|---|---|---|---|---|
| Calculated | 60.32 | 6.47 | 5.30 | 23.45 |
| Found | 60.13 | 6.50 | 5.01 | 23.46 |

EXAMPLE 36

N-Cyano-N'-[2-[4-(6-fluoro-1,2-benzisoxazol-3-yl]1-[1-piperidinyl]ethyl]-N'''-methylguanidine (a)

3-[1-(2-Aminoethyl)-4-piperidinyl]-6-fluoro-1,2-benzisoxazole

A solution of 3.0 g (0.0116 moles) of [4-(6-fluoro-1,2-benzisoxazol-3-yl)-1-piperidinyl]acetonitrile [prepared according to J. T. Strupczewski et al., U.S. Pat. No. 4,355,037; C.A. (1983) 98, 53870p] in 50 ml of tetrahydrofuran is added dropwise at 15° C. to a suspension of 1.3 g (0.034 moles) of lithium aluminium hydride in 85 ml of tetrahydrofuran. The reaction mixture is stirred under nitrogen atmosphere for 20 hours. After cooling to about 15° C., the excess metal hydride is destroyed by adding 20 ml of ethyl acetate and then 20 ml of water. The hydroxides formed are filtered off and washed with methylene chloride. The filtrate and the wash solutions are combined, washed with brine and dried over sodium sulfate and concentrated to dryness under reduced pressure. The residue obtained is used in the next stage without other purification. It is identical with the product obtained in paragraph b of Example 18. Yld: 2.8 g (92%).

(b)

N-Cyano-N'-[2-[4-(6-fluoro-1,2-benzisoxazol-3-yl)-1-piperidinyl]ethyl]-S-methylisothiourea Obtained by operating as in paragraph c of Example 35 starting with 1.7 g (0.0065 moles) of 3-[1-(2-aminoethyl)-4-piperidinyl]-6-fluoro-1,2-benzisoxazole in 50 ml of ethanol and with 0.95 g (0.0065 moles) of dimethyl N-cyanocarbonimidodithioate in 50 ml of ethanol. Chromatography eluent: methylene chloride/methanol: 95/5. Evaporation of the eluate yields a product identical with that obtained in paragraph c of Example 18. Yld: 1.2 g (51%).

(c)

N-Cyano-N'-[2-[4-(6-fluoro-1,2-benzisoxazol-3-yl)-1-piperidinyl]ethyl]-N'''-methylguanidine Obtained by operating as in paragraph d of Example 35 starting with 1.2 g (0.0033 moles) of N-cyano-N'-[2-

We claim:

1. A piperidine which have the formula

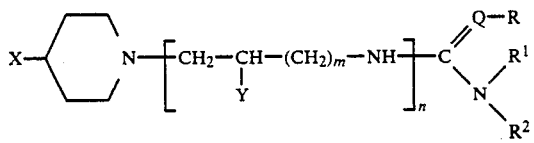

in which X the 4-fluorobenzoyl, 2-(4-fluorophenyl)-1,3-dioxolan-2-yl or 6-fluoro-1,2-benzisoxazol-3-yl group, Y is a hydrogen atom or the hydroxyl group, m is an integer between 0 and 4 inclusive, n is 0 or 1, Q is a nitrogen atom or the methine group; when Q is a nitrogen atom, R is the cyano group or the carbamoyl group; when Q is the methine group, R is the nitro group; $R^1$ and $R^2$ may be identical or different and are hydrogen, a lower alkyl radical, the phenyl radical or the 2,2,2-trifluoroethyl or 2-[4-(4-fluorobenzoyl)-1-piperidinyl]ethyl group; or the $NR^1R^2$ structural unit is the piperidino radical or the 4-(4-fluorobenzoyl)-1-piperidinyl group; or their pharmaceutically acceptable inorganic or organic acid salts.

2. A piperidines as claimed in claim 1, in which X is the 4-fluorobenzoyl or 6-fluoro-1,2-benzisoxazol-3-yl group, Y is a hydrogen atom, m is equal to 0, 1 or 2 and n is equal to 1; and their pharmaceutically acceptable inorganic or organic acid salts.

3. A piperidine as claimed in claim 1, N-cyano-N'-[2-[4-(4-fluorobenzoyl)-1-piperidinyl]ethyl]-N''-methylguanidine, or its pharmaceutically acceptable inorganic or organic acid salts.

4. A piperidine as claimed in claim 1, N-cyano-N'-[2-[4-(6-fluoro-1,2-benzisoxazol-3-yl)-1-piperidinyl]ethyl]-N''-methylguanidine, or its pharmaceutically acceptable inorganic or organic acid salts.

5. A piperidine as claimed in claim 1, N-cyano-N'-[3-[4-(6-fluoro-1,2-benzisoxazol-3-yl)-1-piperidinyl]propyl]-N''-methylguanidine, or its pharmaceutically acceptable inorganic or organic acid salts. acceptable inorganic or organic acid salts.

6. A piperidine as claimed in claim 1, N-cyano-N'-ethyl-N''-[3-[4-(6-fluoro-1,2-benzisoxazol-3-yl)-1-piperidinyl]propyl]guanidine, or its pharmaceutically acceptable inorganic or organic acid salts.

7. A piperidine as claimed in claim 1, N'-cyano-N,N-dimethyl-N''-[3-[4-(6-fluoro-1,2-benzisoxazol-3-yl)-1-piperidinyl]propyl]guanidine, or its pharmaceutically acceptable inorganic or organic acid salts.

8. A piperidine as claimed in claim 1, N-cyano-N'-[3-[4-(6-fluoro-1,2-benzisoxazol-3-yl)-1-piperidinyl]propyl]guanidine, or its pharmaceutically acceptable inorganic or organic acid salts.

9. A piperidine as claimed in claim 1, N-[2-[4-(6-fluoro-1,2-benzisoxazol-3-yl)-1-piperidinyl]ethyl]-N'-methyl-2-nitro-1,1-ethenediamine.

10. A pharmaceutical composition comprising a pharmaceutical carrier and, as active principle, an amount sufficient for pharmaceutical activity of a piperidine which have the formula:

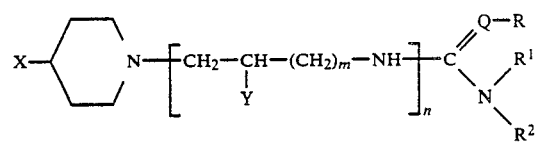

in which X the 4-fluorobenzoyl, 2-(4-fluorophenyl)-1,3-dioxolan-2-yl or 6-fluoro-1,2-benzisoxazol-3-yl group, Y is a hydrogen atom or the hydroxyl group, m is an integer between 0 and 4 inclusive, n is 0 or 1, Q is a nitrogen atom or the methine group; when Q is a nitrogen atom, R is the cyano group or the carbamoyl group; when Q is the methine group, R is the nitro group; $R^1$ and $R^2$ may be identical or different and are hydrogen, a lower alkyl radical, the phenyl radical or the 2,2,2-trifluoroethyl or 2-[4-(4-fluorobenzoyl)-1-piperidinyl]ethyl group; or the $NR^1R^2$ structural unit is the piperidino radical or the 4-(4-fluorobenzoyl)-1-piperidinyl group; or their pharmaceutically acceptable inorganic or organic acid salts.

11. A process for the treatment and prophylaxis of an hypertensive disease and of disorders engendered or aggravated by an excess of serotonin, said process comprising administering to a mammalian an effective amount of, to treat said hypertensive disease or said disorders, said compounds of claim 1.

12. The process of claim 11 wherein said compound is orally administered at a daily dosage of 2 to 100 mg.

13. The process of claim 11 wherein a compounds is intravenously administered at a daily dosage of 0, 2 to 10 mg.

14. A pharmaceutical composition according to claim 10, in which the carrier is suitable for compositions in the form of tablets, coated tablets, gelatin capsules or injectable solution.

15. A piperidine as claimed in claim 1 of the formula:

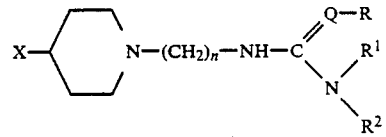

wherein m is 2–6.

16. A piperidine as claimed in claim 15 wherein Q is a nitrogen atom and R is cyano or carbomoyl.

* * * * *